(12) United States Patent
Bruckheimer et al.

(10) Patent No.: US 12,138,185 B2
(45) Date of Patent: *Nov. 12, 2024

(54) PULMONARY ARTERY IMPLANT APPARATUS AND METHODS OF USE THEREOF

(71) Applicant: Restore Medical Ltd., Or Yehuda (IL)

(72) Inventors: Elchanan Bruckheimer, Zikhron-Yaakov (IL); Tanhum Feld, Moshav Merhavia (IL); Gil Naor, Hofit (IL); Stephen F. Bellomo, Zichron Yakov (IL)

(73) Assignee: Restore Medical Ltd., Or Yehuda (IL)

( * ) Notice: Subject to any disclaimer, the term of this patent is extended or adjusted under 35 U.S.C. 154(b) by 662 days.

This patent is subject to a terminal disclaimer.

(21) Appl. No.: 17/373,985

(22) Filed: Jul. 13, 2021

(65) Prior Publication Data

US 2021/0338465 A1  Nov. 4, 2021

Related U.S. Application Data

(63) Continuation of application No. 16/888,872, filed on Jun. 1, 2020, now Pat. No. 11,717,425, which is a
(Continued)

(51) Int. Cl.
*A61F 2/24* (2006.01)
*A61B 17/12* (2006.01)
(Continued)

(52) U.S. Cl.
CPC ........ *A61F 2/915* (2013.01); *A61B 17/12036* (2013.01); *A61B 17/12104* (2013.01);
(Continued)

(58) Field of Classification Search
CPC .. A61F 2/915; A61F 2/06; A61F 2/848; A61F 2002/061; A61F 2/2418;
(Continued)

(56) References Cited

U.S. PATENT DOCUMENTS

| | | |
|---|---|---|
| 3,730,186 A | 5/1973 | Edmunds, Jr. et al. |
| 4,183,102 A | 1/1980 | Guiset |

(Continued)

FOREIGN PATENT DOCUMENTS

| | | |
|---|---|---|
| CA | 2 970 237 | 6/2016 |
| CN | 1430490 | 7/2003 |

(Continued)

OTHER PUBLICATIONS

Notice of Allowance Dated Mar. 18, 2022 from US Patent and Trademark Office Re. U.S. Appl. No. 16/616,465. (22 pages).

(Continued)

*Primary Examiner* — Alvin J Stewart

(57) ABSTRACT

The present invention relates to an implantable apparatus and methods of use thereof for treating congestive heart failure. An apparatus of this invention may be anchored by implantation of a section of the apparatus within in a branch pulmonary artery, for example the left pulmonary artery, which then positions and anchors another section, for example a device frame section of the apparatus within the main pulmonary artery. A medical device may be attached to the anchored device frame.

22 Claims, 17 Drawing Sheets

Related U.S. Application Data continuation of application No. 15/327,075, filed as application No. PCT/IL2015/050745 on Jul. 20, 2015, now Pat. No. 10,667,931.

(60) Provisional application No. 62/026,656, filed on Jul. 20, 2014.

(51) Int. Cl.

| | |
|---|---|
| A61F 2/06 | (2013.01) |
| A61F 2/848 | (2013.01) |
| A61F 2/856 | (2013.01) |
| A61F 2/915 | (2013.01) |
| A61F 2/954 | (2013.01) |
| A61F 2/82 | (2013.01) |

(52) U.S. Cl.
CPC .......... *A61B 17/12136* (2013.01); *A61F 2/06* (2013.01); *A61F 2/2421* (2013.01); *A61F 2/848* (2013.01); *A61F 2/856* (2013.01); *A61F 2/954* (2013.01); *A61F 2002/061* (2013.01); *A61F 2002/065* (2013.01); *A61F 2002/068* (2013.01); *A61F 2002/825* (2013.01); *A61F 2002/828* (2013.01); *A61F 2002/8486* (2013.01); *A61F 2002/91508* (2013.01); *A61F 2002/91575* (2013.01); *A61F 2230/0065* (2013.01); *A61F 2250/0039* (2013.01); *A61F 2250/0067* (2013.01)

(58) Field of Classification Search
CPC ............. A61F 2/2478; A61F 2002/068; A61B 5/6862; A61B 5/02158
See application file for complete search history.

(56) References Cited

U.S. PATENT DOCUMENTS

| | | | |
|---|---|---|---|
| 4,425,908 A | 1/1984 | Simon | |
| 4,601,718 A | 7/1986 | Possis et al. | |
| 4,950,276 A | 8/1990 | Vince | |
| 5,156,620 A | 10/1992 | Pigott | |
| 5,167,628 A | 12/1992 | Boyles | |
| 5,330,528 A | 7/1994 | Lazim | |
| 5,332,403 A | 7/1994 | Kolff | |
| 5,383,892 A | 1/1995 | Cardon et al. | |
| 5,423,851 A | 6/1995 | Samuels | |
| 5,554,180 A | 9/1996 | Turk | |
| 5,554,185 A | 9/1996 | Block et al. | |
| 5,618,301 A | 4/1997 | Hauenstein et al. | |
| 5,662,711 A * | 9/1997 | Douglas | A61F 2/06 604/9 |
| 5,683,411 A | 11/1997 | Kavteladze et al. | |
| 5,755,779 A | 5/1998 | Horiguchi | |
| 6,120,534 A * | 9/2000 | Ruiz | A61F 2/86 623/1.3 |
| 6,312,462 B1 | 11/2001 | McDermott et al. | |
| 6,471,635 B1 | 10/2002 | Forsell | |
| 6,533,800 B1 | 3/2003 | Barbut | |
| 6,562,066 B1 | 5/2003 | Martin | |
| 6,595,980 B1 | 7/2003 | Barbut | |
| 6,616,624 B1 | 9/2003 | Kieval | |
| 6,638,257 B2 | 10/2003 | Amplatz | |
| 6,790,230 B2 | 9/2004 | Beyersdorf et al. | |
| 6,936,057 B1 | 8/2005 | Nobles | |
| 6,953,476 B1 | 10/2005 | Shalev | |
| 7,001,409 B2 | 2/2006 | Amplatz | |
| 7,128,750 B1 | 10/2006 | Stergiopulos | |
| 7,158,832 B2 | 1/2007 | Kieval et al. | |
| 7,201,772 B2 | 4/2007 | Schwammenthal et al. | |
| 7,331,993 B2 | 2/2008 | White | |
| 7,442,204 B2 | 10/2008 | Schwammenthal et al. | |
| 7,497,873 B1 | 3/2009 | Bruckheimer | |
| 7,670,367 B1 | 3/2010 | Chouinard et al. | |
| 7,862,502 B2 | 1/2011 | Pool et al. | |
| 7,935,144 B2 | 5/2011 | Robin et al. | |
| 7,983,765 B1 | 7/2011 | Doan et al. | |
| 7,998,220 B2 | 8/2011 | Murphy | |
| 8,070,708 B2 | 12/2011 | Rottenberg et al. | |
| 8,091,556 B2 | 1/2012 | Keren et al. | |
| 8,556,954 B2 | 10/2013 | Ben MuVhar et al. | |
| 8,597,349 B2 | 12/2013 | Alkhatib | |
| 8,663,314 B2 | 3/2014 | Wood et al. | |
| 8,696,611 B2 | 4/2014 | Nitzan et al. | |
| 8,764,772 B2 | 7/2014 | Tekulve | |
| 8,808,356 B2 | 8/2014 | Braido et al. | |
| 8,858,612 B2 | 10/2014 | Ben-Muvhar et al. | |
| 8,911,489 B2 | 12/2014 | Ben-Muvhar | |
| 8,940,040 B2 | 1/2015 | Shariari | |
| 9,034,034 B2 | 5/2015 | Nitzan et al. | |
| 9,125,567 B2 | 9/2015 | Gross et al. | |
| 9,393,384 B1 | 7/2016 | Kapur et al. | |
| 9,474,839 B2 | 10/2016 | Oran et al. | |
| 9,532,868 B2 | 1/2017 | Braido | |
| 9,572,661 B2 | 2/2017 | Robin et al. | |
| 9,603,708 B2 | 3/2017 | Robin et al. | |
| 9,629,715 B2 * | 4/2017 | Nitzan | A61F 2/2412 |
| 9,649,480 B2 * | 5/2017 | Sugimoto | A61F 2/2436 |
| 9,668,861 B2 | 6/2017 | McGuckin, Jr. | |
| 9,681,948 B2 | 6/2017 | Levi et al. | |
| 9,681,949 B2 | 6/2017 | Braido et al. | |
| 9,687,242 B2 | 6/2017 | Hendriksen et al. | |
| 9,707,382 B2 * | 7/2017 | Nitzan | A61M 27/006 |
| 9,713,696 B2 | 7/2017 | Yacoby et al. | |
| 9,724,499 B2 | 8/2017 | Rottenberg et al. | |
| 9,744,059 B2 | 8/2017 | Ben-Muvhar | |
| 9,775,636 B2 | 10/2017 | Fazio et al. | |
| 9,849,006 B2 * | 12/2017 | Kozyak | A61F 2/90 |
| 10,010,328 B2 | 7/2018 | Cragg | |
| 10,022,128 B2 | 7/2018 | Bödewadt et al. | |
| 10,492,933 B2 | 12/2019 | Jenni | |
| 10,568,634 B2 | 2/2020 | Goldie et al. | |
| 10,667,931 B2 * | 6/2020 | Bruckheimer | A61F 2/2421 |
| 10,835,394 B2 | 11/2020 | Nae et al. | |
| 10,912,645 B2 * | 2/2021 | Rottenberg | A61B 5/0215 |
| 11,135,054 B2 | 10/2021 | Nitzan et al. | |
| 11,224,503 B2 | 1/2022 | Karavany et al. | |
| 11,234,702 B1 * | 2/2022 | Eigler | A61B 5/0215 |
| 11,253,685 B2 | 2/2022 | Fahey et al. | |
| 11,357,610 B2 | 6/2022 | Karavany et al. | |
| 11,364,132 B2 * | 6/2022 | Bellomo | A61F 2/07 |
| 11,717,425 B2 * | 8/2023 | Bruckheimer | A61F 2/856 623/1.14 |
| 11,883,030 B2 * | 1/2024 | Quadri | A61B 17/12109 |
| 2001/0053330 A1 | 12/2001 | Ozaki | |
| 2002/0107536 A1 | 8/2002 | Hussein | |
| 2003/0032976 A1 | 2/2003 | Boucek | |
| 2003/0097172 A1 | 5/2003 | Shalev et al. | |
| 2003/0144575 A1 * | 7/2003 | Forsell | A61F 2/0036 600/29 |
| 2003/0149473 A1 | 8/2003 | Chouinard et al. | |
| 2003/0167068 A1 | 9/2003 | Amplatz | |
| 2003/0236568 A1 | 12/2003 | Hojeibane et al. | |
| 2004/0077988 A1 | 4/2004 | Tweden et al. | |
| 2004/0111006 A1 * | 6/2004 | Alferness | A61M 60/295 600/16 |
| 2004/0176672 A1 * | 9/2004 | Silver | A61B 5/14532 600/364 |
| 2004/0236412 A1 | 11/2004 | Brar et al. | |
| 2005/0055082 A1 | 3/2005 | Ben Muvhar et al. | |
| 2005/0096734 A1 | 5/2005 | Majercak et al. | |
| 2005/0148925 A1 | 7/2005 | Rottenberg et al. | |
| 2005/0165344 A1 | 7/2005 | Dobak, III | |
| 2005/0171556 A1 | 8/2005 | Murphy | |
| 2005/0182483 A1 | 8/2005 | Osborne et al. | |
| 2005/0234388 A1 | 10/2005 | Amos et al. | |
| 2005/0273160 A1 | 12/2005 | Lashinski et al. | |
| 2006/0009800 A1 | 1/2006 | Christianson et al. | |
| 2006/0025855 A1 | 2/2006 | Lashinski et al. | |
| 2006/0030920 A1 | 2/2006 | Ben-Muvhar | |
| 2006/0106449 A1 | 5/2006 | Ben Muvhar | |
| 2006/0106450 A1 | 5/2006 | Ben Muvhar | |
| 2006/0122692 A1 | 6/2006 | Gilad et al. | |

(56) References Cited

U.S. PATENT DOCUMENTS

| | | |
|---|---|---|
| 2006/0149360 A1 | 7/2006 | Schwammenthal et al. |
| 2006/0178740 A1 | 8/2006 | Stacchino et al. |
| 2006/0241745 A1 | 10/2006 | Solem |
| 2007/0038259 A1* | 2/2007 | Kieval ............... A61N 1/36114 607/44 |
| 2007/0043435 A1 | 2/2007 | Seguin et al. |
| 2007/0129637 A1* | 6/2007 | Wolinsky ........... A61B 5/02152 600/549 |
| 2007/0179590 A1 | 8/2007 | Lu et al. |
| 2007/0198097 A1 | 8/2007 | Zegdi |
| 2007/0213813 A1 | 9/2007 | Von Segesser et al. |
| 2008/0027268 A1 | 1/2008 | Buckner |
| 2008/0097497 A1* | 4/2008 | Assad .................. A61B 17/12 606/157 |
| 2008/0140110 A1 | 6/2008 | Spence |
| 2008/0176271 A1* | 7/2008 | Silver .................... A61B 5/413 422/68.1 |
| 2008/0194905 A1* | 8/2008 | Walsh .................. A61M 60/869 600/17 |
| 2008/0208329 A1 | 8/2008 | Bishop et al. |
| 2008/0275350 A1* | 11/2008 | Liao .................... A61B 5/6882 600/486 |
| 2009/0099653 A1 | 4/2009 | Suri et al. |
| 2009/0112312 A1 | 4/2009 | LaRose et al. |
| 2009/0149950 A1 | 6/2009 | Wampler |
| 2009/0198315 A1 | 8/2009 | Boudjemline |
| 2009/0270974 A1 | 10/2009 | Berez |
| 2010/0023046 A1 | 1/2010 | Heidner et al. |
| 2010/0057192 A1 | 3/2010 | Celermajer |
| 2010/0125288 A1* | 5/2010 | Gelfand ............... A61B 5/6846 606/158 |
| 2010/0185277 A1 | 7/2010 | Braido et al. |
| 2010/0222633 A1 | 9/2010 | Poirier |
| 2010/0249911 A1 | 9/2010 | Alkhatib |
| 2010/0286758 A1 | 11/2010 | Berglund |
| 2011/0021864 A1 | 1/2011 | Criscione et al. |
| 2011/0046710 A1 | 2/2011 | Mangiardi et al. |
| 2011/0054589 A1 | 3/2011 | Bashiri et al. |
| 2011/0071624 A1 | 3/2011 | Finch et al. |
| 2011/0098800 A1 | 4/2011 | Braido et al. |
| 2011/0098802 A1 | 4/2011 | Braido et al. |
| 2011/0213408 A1 | 9/2011 | Gross et al. |
| 2011/0264194 A1* | 10/2011 | Griswold ............. A61B 5/6862 600/300 |
| 2011/0306916 A1 | 12/2011 | Nitzan et al. |
| 2012/0101572 A1 | 4/2012 | Kovalsky et al. |
| 2012/0123195 A1 | 5/2012 | Woodruff et al. |
| 2012/0123556 A1 | 5/2012 | Durgin |
| 2012/0149978 A1 | 6/2012 | Olivera et al. |
| 2012/0165928 A1* | 6/2012 | Nitzan .................. A61F 2/2415 623/2.15 |
| 2012/0310323 A1 | 12/2012 | Roeder |
| 2013/0073026 A1 | 3/2013 | Russo et al. |
| 2013/0096580 A1 | 4/2013 | Cohn et al. |
| 2013/0103162 A1 | 4/2013 | Costello |
| 2013/0172981 A1 | 7/2013 | Gross et al. |
| 2013/0178750 A1* | 7/2013 | Sheehan ............... A61B 5/0215 604/9 |
| 2013/0261531 A1 | 10/2013 | Gallagher et al. |
| 2013/0274648 A1* | 10/2013 | Weinberger ......... A61M 1/3655 604/9 |
| 2014/0012181 A1 | 1/2014 | Sugimoto et al. |
| 2014/0039537 A1* | 2/2014 | Carrison ........... A61B 17/12045 606/191 |
| 2014/0107768 A1* | 4/2014 | Venkatasubramanian .................. A61B 5/6862 623/2.11 |
| 2014/0128957 A1 | 5/2014 | Losordo et al. |
| 2014/0155997 A1* | 6/2014 | Braido .................. A61F 2/2409 623/2.37 |
| 2014/0276141 A1* | 9/2014 | Dlugach ................ A61F 2/95 600/300 |
| 2014/0277425 A1 | 9/2014 | Dakin |
| 2014/0303710 A1 | 10/2014 | Zhang et al. |
| 2014/0324094 A1* | 10/2014 | Weber .................. A61B 5/0816 606/198 |
| 2014/0350565 A1 | 11/2014 | Yacoby |
| 2014/0350668 A1 | 11/2014 | Delaloye et al. |
| 2014/0364686 A1 | 12/2014 | McClurg |
| 2015/0073544 A1 | 3/2015 | Gorman, III et al. |
| 2015/0148896 A1 | 5/2015 | Karapetian et al. |
| 2015/0174308 A1 | 6/2015 | Oran et al. |
| 2016/0000590 A1* | 1/2016 | Boyden ................ A61B 5/6862 600/12 |
| 2016/0022447 A1* | 1/2016 | Kim ................... A61B 5/02158 623/1.15 |
| 2016/0038087 A1* | 2/2016 | Hunter ................ A61B 5/0205 623/1.1 |
| 2016/0151153 A1 | 6/2016 | Sandstrom et al. |
| 2016/0296317 A1 | 10/2016 | Timmermans et al. |
| 2017/0042551 A1 | 2/2017 | Celermajer et al. |
| 2017/0065402 A1* | 3/2017 | Tozzi .................. A61M 60/148 |
| 2017/0113026 A1 | 4/2017 | Finch |
| 2017/0172771 A1 | 6/2017 | Bruckjeimer et al. |
| 2017/0215885 A1* | 8/2017 | Goldie ................ A61M 29/02 |
| 2017/0216025 A1 | 8/2017 | Nitzan et al. |
| 2017/0325946 A1 | 11/2017 | Bell et al. |
| 2017/0340441 A1 | 11/2017 | Rowe |
| 2017/0340460 A1* | 11/2017 | Rosen ..................... A61F 2/07 |
| 2017/0367855 A1* | 12/2017 | Jenni ....................... A61F 2/90 |
| 2018/0021156 A1 | 1/2018 | Ben-Muvhar et al. |
| 2018/0036109 A1* | 2/2018 | Karavany ............... A61F 2/852 |
| 2018/0085128 A1* | 3/2018 | Bellomo .......... A61B 17/12172 |
| 2018/0092732 A1 | 4/2018 | Kringle |
| 2019/0000483 A1 | 1/2019 | Mogensen |
| 2019/0159684 A1* | 5/2019 | Bozsak ................ A61B 5/4851 |
| 2019/0183354 A1* | 6/2019 | Rowe .................... A61B 5/741 |
| 2019/0307459 A1 | 10/2019 | Celermajer et al. |
| 2019/0335998 A1* | 11/2019 | Caruso ................ A61B 5/0031 |
| 2020/0000582 A1 | 1/2020 | Lashinski et al. |
| 2020/0205962 A1 | 7/2020 | Karavant et al. |
| 2020/0229956 A1 | 7/2020 | Jackson et al. |
| 2020/0289299 A1 | 9/2020 | Bruckheimer et al. |
| 2020/0297516 A1 | 9/2020 | Bellomo et al. |
| 2020/0352696 A1 | 11/2020 | Radhakrishnan et al. |
| 2020/0360024 A1 | 11/2020 | Bellomo et al. |
| 2020/0397320 A1* | 12/2020 | Gleich ................ A61B 5/6847 |
| 2021/0161643 A1 | 6/2021 | Totten et al. |
| 2021/0169634 A1 | 6/2021 | Karavany et al. |
| 2021/0290358 A1 | 9/2021 | Goodman et al. |
| 2022/0008014 A1* | 1/2022 | Rowe .................. A61B 5/6862 |
| 2022/0015889 A1 | 1/2022 | Lima et al. |
| 2022/0022881 A1 | 1/2022 | Celermajer et al. |
| 2022/0039752 A1* | 2/2022 | Hunter ................ A61B 5/0031 |
| 2022/0039938 A1 | 2/2022 | Karavany et al. |
| 2022/0117765 A1 | 4/2022 | Yacoby et al. |
| 2022/0241063 A1 | 8/2022 | Karavany et al. |
| 2022/0287580 A1* | 9/2022 | Yeo .................... A61B 5/02444 |
| 2022/0346709 A1* | 11/2022 | Mittal .................. A61B 5/4851 |
| 2023/0218180 A1* | 7/2023 | Mujeeb-U-Rahman ...................... A61B 5/4851 623/2.17 |
| 2023/0404432 A1* | 12/2023 | Sabczynski .......... A61B 5/6862 |
| 2023/0414177 A1* | 12/2023 | Valdez ................ A61B 5/6882 |
| 2024/0023896 A1* | 1/2024 | Enomoto ............. A61B 5/0031 |

FOREIGN PATENT DOCUMENTS

| | | |
|---|---|---|
| CN | 1672644 | 9/2005 |
| CN | 101687088 | 3/2010 |
| CN | 102764170 | 11/2012 |
| CN | 102961200 | 3/2013 |
| CN | 103202735 | 7/2013 |
| CN | 103930042 | 7/2014 |
| CN | 204106100 | 1/2015 |
| CN | 105392431 | 3/2016 |
| DE | 10102045 | 1/2003 |
| EP | 1576929 | 9/2005 |
| EP | 1849440 | 10/2007 |
| EP | 1870057 | 12/2007 |
| EP | 2567663 | 3/2013 |

(56) References Cited

FOREIGN PATENT DOCUMENTS

| | | |
|---|---|---|
| EP | 3300672 | 4/2018 |
| WO | WO 2001/035861 | 5/2001 |
| WO | WO 03/028522 | 4/2003 |
| WO | WO2003/028522 | 4/2003 |
| WO | WO 2005/084730 | 9/2005 |
| WO | WO 2006/131930 | 12/2006 |
| WO | WO2007/129220 | 11/2007 |
| WO | WO2007/144782 | 12/2007 |
| WO | WO 2011/156176 | 12/2011 |
| WO | WO 2013/096548 | 6/2013 |
| WO | WO 2016/013006 | 1/2016 |
| WO | WO 2016/096529 | 6/2016 |
| WO | WO 2017/024357 | 2/2017 |
| WO | WO 2017/194437 | 11/2017 |
| WO | WO 2018/225059 | 12/2018 |
| WO | WO 2020/023512 | 1/2020 |
| WO | WO 2020/109979 | 6/2020 |
| WO | WO 2023/281507 | 1/2023 |

OTHER PUBLICATIONS

English Summary Dated Mar. 17, 2022 of Notification of Office Action and Search Report Dated Mar. 9, 2022 From the State Intellectual Property Office of the People's Republic of China Re. Application No. 201880036104.4. (2 Pages).
Notification of Office Action and Search Report Dated Mar. 9, 2022 From the State Intellectual Property Office of the People's Republic of China Re. Application No. 201880036104.4. (8 Pages).
International Search Report and the Written Opinion Dated Oct. 12, 2022 From the International Searching Authority Re. Application No. PCT/IL2022/050724. (15 Pages).
Office Action Dated Jul. 13, 2022 From the Israel Patent Office Re. Application No. 250181. (5 Pages).
Translation Dated Jul. 20, 2022 of Office Action Dated Jul. 13, 2022 From the Israel Patent Office Re. Application No. 250181. (4 Pages).
Notice of Allowance Dated Jun. 6, 2023 Together With Inteview Summary Dated May 22, 2023 from the US Patent and Trademark Office Re. U.S. Appl. No. 15/716,667. (22 pages).
International Preliminary Report on Patentability Dated Jan. 24, 2017 From the International Bureau of WIPO Re. Application No. PCT/IL2015/050745. (8 Pages).
International Search Report and the Written Opinion Dated Nov. 5, 2015 From the International Searching Authority Re. Application No. PCT/IL2015/050745. (14 Pages).
Notice of Allowance Dated Jan. 24, 2020 From the US Patent and Trademark Office Re. U.S. Appl. No. 15/327,075. (8 pages).
Office Action Dated Jun. 7, 2021 From the Israel Patent Office Re. Application No. 250181 and Its Translation Into English. (7 Pages).
Office Action Dated May 12, 2020 From the Israel Patent Office Re. Application No. 250181 and Its Translation Into English. (7 Pages).
Official Action Dated Feb. 2, 2018 From the US Patent and Trademark Office Re. U.S. Appl. No. 15/327,075. (15 pages).
Official Action Dated Jun. 5, 2019 From the US Patent and Trademark Office Re. U.S. Appl. No. 15/327,075. (6 Pages).
Official Action Dated Sep. 6, 2018 From the US Patent and Trademark Office Re. U.S. Appl. No. 15/327,075. (9 pages).
Official Action Dated Dec. 20, 2018 From the US Patent and Trademark Office Re. U.S. Appl. No. 15/327,075. (12 pages).
Official Action Dated Sep. 27, 2019 From the US Patent and Trademark Office Re. U.S. Appl. No. 15/327,075. (6 Pages).
Supplementary European Search Report and the European Search Opinion Dated Feb. 9, 2018 From the European Patent Office Re. Application No. 15825239.5. (7 Pages).
Bailey "Back to the Future! Bold New Indication for Pulmonary Artery Banding", The Journal of Heart and Lung Transplantation, 32(5): 482-483, May 1, 2013.
Schranz et al. "Pulmonary Artery Banding in Infants and Young Children With Lleft Ventricular Dilated Cardiomyopathy: A Novel Therapeutic Strategy Before Heart Transplantation", The Journal of Heart and Lung Transplantation, 32(5):475- 481, May 31, 2013.
Office Action Dated Jun. 20, 2023 From the Israel Patent Office Re. Application No. 271184. (4 Pages).
Notice of Allowance Dated Sep. 15, 2023 from the US Patent and Trademark Office Re. U.S. Appl. No. 16/984,166. (15 pages).
Official Action Dated Aug. 16, 2022 from US Patent and Trademark Office Re. U.S. Appl. No. 16/888,872. (43 pages).
Communication Pursuant to Article 94(3) EPC Dated May 24, 2023 From the European Patent Office Re. Application No. 17193799.8. (4 Pages).
International Preliminary Report on Patentability Dated Jan. 18, 2024 From the International Bureau of WIPO Re. Application No. PCT/IL2022/050724 (9 Pages).
Notification of Office Action and Search Report Dated Nov. 30, 2021 From the State Intellectual Property Office of the People's Republic of China Re. Application No. 201710896715.3 and Its Summary in English.
Interview Summary Dated Apr. 13, 2022 from US Patent and Trademark Office Re. U.S. Appl. No. 15/716,667. (2 pages).
Notice of Allowance Dated Mar. 22, 2023 from the US Patent and Trademark Office Re. U.S. Appl. No. 16/888,872. (16 pages).
Santamore et al. "Ventricular Interdependence: Significant Left Ventricular Contributions to Right Ventricular Systolic Function", Progress in Cardiovascular Diseases, 40(4): 289-308, Jan./Feb. 1998.
Official Action Dated Apr. 5, 2023 from the US Patent and Trademark Office Re. U.S. Appl. No. 16/984,166. (25 pages).
Final Official Action Dated Feb. 22, 2022 from US Patent and Trademark Office Re. U.S. Appl. No. 15/716,667. (23 pages).
Advisory Action Dated Jun. 29, 2022 from US Patent and Trademark Office Re. U.S. Appl. No. 15/716,667. (8 pages).
Official Action Dated Oct. 14, 2022 from the US Patent and Trademark Office Re. U.S. Appl. No. 15/716,667. (24 pages).
Official Action Dated Oct. 18, 2022 from the US Patent and Trademark Office Re. U.S. Appl. No. 16/984,166. (55 pages).
Office Action Dated Oct. 30, 2022 From the Israel Patent Office Re. Application No. 271184. (4 Pages).
Communication Pursuant to Article 94(3) EPC Dated Jan. 3, 2020 From the European Patent Office Re. Application No. 17193799.8. (4 Pages).
European Search Report and the European Search Opinion Dated Jan. 19, 2018 From the European Patent Office Re. Application No. 17193799.8. (9 Pages).
Final Official Action Dated Jul. 2, 2020 from the US Patent and Trademark Office Re. U.S. Appl. No. 15/716,667. (16 pages).
Final Official Action Dated Dec. 21, 2021 from US Patent and Trademark Office Re. U.S. Appl. No. 16/616,465. (6 pages).
International Preliminary Report on Patentability Dated Dec. 19, 2019 From the International Bureau of WIPO Re. Application No. PCT/IL2018/050604. (9 Pages).
International Search Report and the Written Opinion Dated Sep. 20, 2018 From the International Searching Authority Re. Application No. PCT/IL2018/050604. (12 Pages).
Office Action Dated Oct. 19, 2020 From the Israel Patent Office Re. Application No. 254791 and Its Translation Into English. (6 Pages).
Official Action Dated Dec. 3, 2019 From the US Patent and Trademark Office Re. U.S. Appl. No. 15/716,667. (18 pages).
Official Action Dated Aug. 13, 2021 from the US Patent and Trademark Office Re. U.S. Appl. No. 15/716,667. (19 pages).
Official Action Dated Jul. 14, 2021 from the US Patent and Trademark Office Re. U.S. Appl. No. 16/616,465. (16 pages).
Restriction Official Action Dated Apr. 30, 2021 From the US Patent and Trademark Office Re. U.S. Appl. No. 16/616,465. (7 Pages).
Supplementary European Search Report and the European Search Opinion Dated Feb. 4, 2021 From the European Patent Office Re. Application No. 18812772.4. (7 Pages).
Ahmadi et al. "Percutaneously Adjustable Pulmonary Artery Band", The Annals of the Thoracic Surgery, 60(6/Suppl.): S520-S522, Dec. 1995.
Amahzoune et al. "A New Endovascular Size Reducer for Large Pulmonary Outflow Tract", European Journal of Cardio-Thoracic Surgery, 37(3): 730-752, Available Online Oct. 2, 2009.

(56) References Cited

OTHER PUBLICATIONS

Basquin et al. "Transcatheter Valve Insertion in a Model of Enlarged Right Ventricular Outflow Tracts", The Journal of Thoracic and Cardiovascular Surgery, 139(1): 198-208, Jan. 2010.
Boudjemline et al. "Percutaneous Pulmonary Valve Replacement in a Large Right Ventricular Outflow Tract. An Experimental Study", Journal of the American College of Cardiology, 43(6): 1082-1087, Mar. 17, 2004.
Boudjemline et al. "Steps Toward the Peercutancous Replacement of Atrioventricular Valves. An Experimental Study", Journal of the American College of Cardiology, 46(2): 360-365, Jul. 19, 2005.
Corno et al. "The Non-Circular Shape of Flo Watch®-PAB Prvents the Need for Pulmonary Artery Reconstruction After Banding. Computational Fluid Dynamics and Clinical Correlations", European Journal of Cardio-Thoracic Surgery, 29(1): 93-99, Available Online Dec. 6, 2005.
DiBardino et al. "A Method of Transcutaneously Adjustable Pulmonary Artery Banding for Staged Left Ventricular Retraining", The Journal of Thoracic and Cardiovascular Surgery, 144(3): 553-556, Published Online Feb. 9, 2012.
Horita et al. "Development of a Reexpandable Covered Stent for Children", Catheterization and Cardiovascular Interventions, 68(5): 727-734, Published Online Oct. 12, 2006.
Le Bret et al. "A New Percutaneously Adjustable, Thoracoscopically Implantable, Pulmonary Artery Banding: An Experimental Study", The Annals of Thoracic Surgery, 72(4): 1358-1361, Oct. 31, 2001.
Mollet et al. "Development of a Device for Transcatheter Pulmonary Artery Banding: Evaluation in Animals", European Heart Journal, 27(24): 3065-3072, Published Ahead of Print Oct. 31, 2006.
Mollet et al. "Off-Pump Replacement of the Pulmonary Valve in Large Right Ventricular Outflow Tracts: A Transcatheter Approach Using an Intravascular Infundibulum Reducer", Pediatric Research, 62(4): 428-433, Oct. 2007.
Nakahata et al. "Percutaneous Bilateral Pulmonary Artery Banding Using a Re-Expandable Covered Stent: Preliminary Animal Study", The Kisato Medical Journal, 41(2): 165-169, Sep. 2011.
Schranz et al. "Pulmonary Artery Banding in Infants and Young Children With Left Ventricular Dilated Cardiomyopathy: A Novel Therapeutic Strategy Before Heart Transplantation", The Journal of Heart and Lung Transplantation, 32(5): 475-481, Published Online Feb. 12, 2013.
Talwar et al. "Changing Outcomes of Pulmonary Artery Banding With the Percutaneoulsy Adjustable Pulmonary Artery Band", The Annals of Thoracic Surgery, 85(2): 593-598, Feb. 2008.
Watanabe et al. "How to Clamp the Main Pulmonary Artery During Video-Assisted Thoracoscopic Surgery Lobectomy", European Journal of Cardio-Thoracic Surgery, 31(1): 129-131, Published Online Nov. 29, 2006.
Notification of Office Action and Dated Jul. 5, 2022 From the State Intellectual Property Office of the People's Republic of China Re. Application No. 201710896715.3 and Its Summary in English. (5 Pages).

* cited by examiner

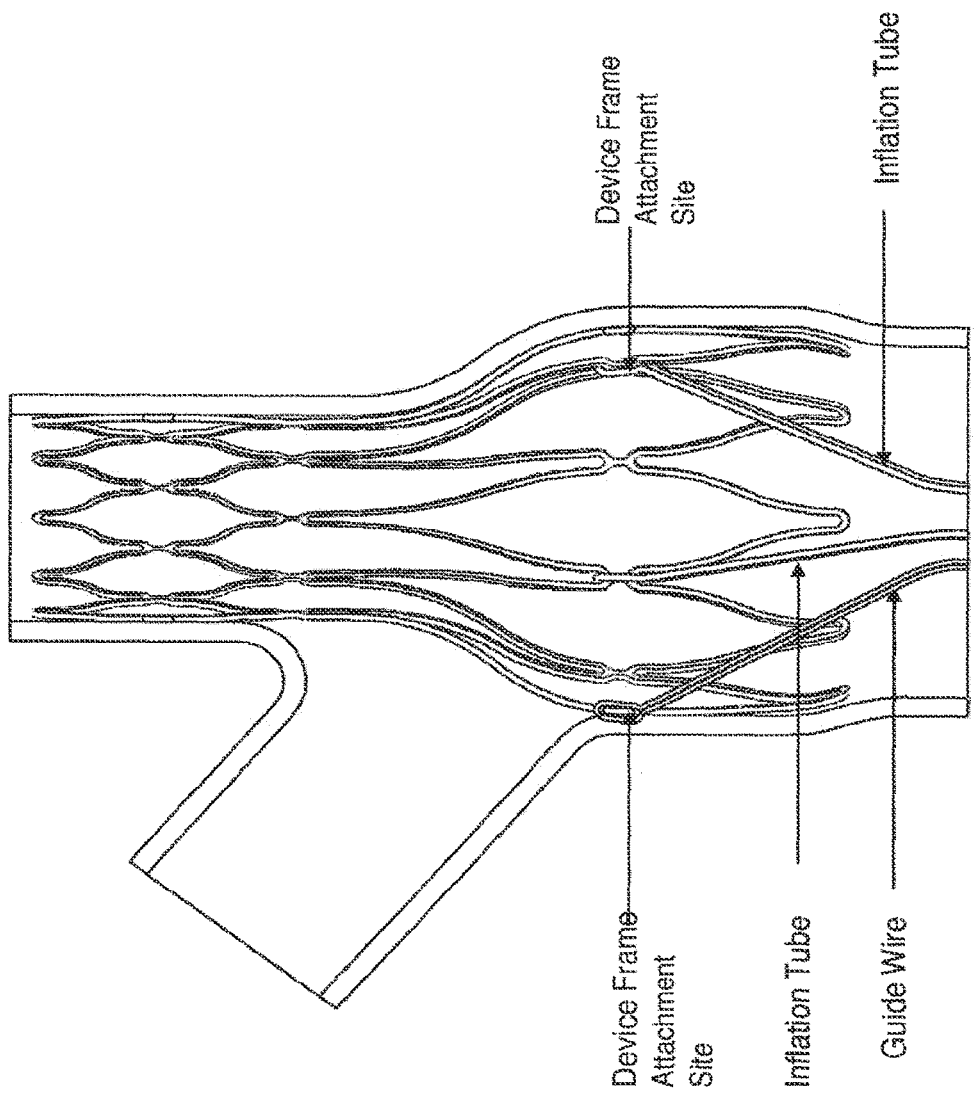

PULMONARY ARTERY IMPLANT APPARATUS AND METHODS OF USE THEREOF

RELATED APPLICATIONS

This application is a continuation of U.S. patent application Ser. No. 16/888,872 filed on Jun. 1, 2020, which is a continuation of U.S. patent application Ser. No. 15/327,075 filed on Jan. 18, 2017, now U.S. Pat. No. 10,667,931, which is a National Phase of PCT Patent Application No. PCT/IL2015/050745 having International Filing Date of Jul. 20, 2015, which claims the benefit of priority under 35 USC § 119(e) of U.S. Provisional Patent Application No. 62/026,656 filed Jul. 20, 2014. The contents of the above applications are all incorporated by reference as if fully set forth herein in their entirety.

FIELD OF INTEREST

The current invention relates to implantable apparatuses for accurately positioning a medical device within the main pulmonary artery, and to methods of use thereof for treating, reducing the severity of, or reducing symptoms associated with, or any combination thereof, congestive heart failure, including left ventricular failure, wherein use may in certain embodiments, affect the position and function of the interventricular septum during systole.

BACKGROUND OF THE INVENTION

Congestive heart failure (CHF) means the heart does not pump out sufficient blood to meet the body's demands. CHF can result from either a reduced ability of the heart muscle to contract (systolic failure) or from a mechanical problem that limits the ability of the heart's chambers to fill with blood (diastolic failure). When weakened, the heart is unable to keep up with the demands placed upon it and the left ventricle (LV) gets backed up or congested—hence the name of the disorder. CHF is a progressive disease. Failure of the left side of the heart (left-heart failure/left-sided failure/left-ventricle failure) is the most common form of the disease.

CHF affects people of all ages including children, but it occurs most frequently in those over age 60, and is the leading cause of hospitalization and death in that age group. Current treatments of CHF include lifestyle changes, medications, and surgery to bypass blocked blood vessels, replace regurgitant or stenotic valves, install stents to open narrowed coronary vessels, install pump assist devices or transplantation of the heart.

Normal cardiac contraction is a finely tuned orchestrated activity dependent on muscle function, ventricular geometry and loading conditions termed preload and afterload. When CHF due to LV systolic failure occurs it is typically associated with changes in the geometry of the ventricles, often called remodeling. The LV becomes dilated and the interventricular septum is deflected into the right ventricle (RV), resulting in decreased LV output/pumping efficiency. Compare FIG. 1A with FIG. 1B. The efficient systolic function of the LV is dependent not only on the strength of the myocardium but also on the LV geometry, the position and shape of the interventricular septum and the geometry and function of the RV. Interventricular dependence has been documented in experimental studies which have evaluated both normal and pathological preparations in animals. LV systolic function can be directly influenced by interventions affecting the RV and the position of the interventricular septum.

Surgical pulmonary artery banding (PAB) is a technique that was described more than 60 years ago and is still in use today for children and infants with congenital heart defects, such as overflow of blood to the lungs and volume overload of the LV. PAB is typically performed through a thoracotomy and involves wrapping a band around the exterior of the main pulmonary artery (MPA) and fixing the band in place, often with the use of sutures. Once applied, the band is tightened, narrowing the diameter of the MPA, increasing resistance to flow, reducing blood flow to the lungs, and reducing downstream pulmonary artery (PA) pressure.

Surgical PAB procedures involve the risks present with all surgical procedures. In addition, use of PAB has a number of particular disadvantages and drawbacks. Primary among these drawbacks is the inability of the surgeon performing the procedure to accurately assess, from the hemodynamic standpoint, the optimal final diameter to which the PA should be adjusted. Often, the surgeon must rely upon his or her experience in adjusting the band to achieve acceptable forward flow while decreasing the blood flow sufficiently to protect the pulmonary vasculature.

It is also not uncommon for the band to migrate towards one of the main pulmonary branches (usually the left), resulting in stenosis of the other main pulmonary branch (usually the right). There have also been reports of hardening of the vessels around the band due to buildup of calcium deposits and scarring of the PA wall beneath the band, which can also inhibit blood flow. Flow resistance due to PAB may change over time, and additional surgeries to adjust band tightness occur in up to one third of patients. The band is typically removed in a subsequent operation, for example, when a congenital malformation is corrected in the child or infant.

In addition to the classical use of PAB for treatment of congenital defects in infants and children, there has been a recent report of use of surgical PAB for left ventricle dilated cardiomyopathy (LVDCM) in infants and young children. This method includes increasing the pressure load on the right ventricle by placing a band around the pulmonary artery. The increased pressure in the right ventricle caused a leftward shift of the interventricular septum and improvement of left ventricle function. It was found that the optimal degree of constriction was achieved when the RV pressure was approximately 60% to 70% of the systemic level and so that the interventricular septum slightly moved to a midline position. The success of these procedures in infants and children has been reported to be possibly due to the potential for myocyte recovery and repopulation being significantly greater for infants and young children than for adults. However, it is the position of the inventors that the geometric improvements to the failing heart due to PAB may be responsible, at least partially, for the observed improvements in LV function, and therefore PAB for adult left ventricle heart failure may demonstrate similar improvement in LV function.

It would be desirable to provide a relatively simple PAB device which could be implanted in a minimally-invasive fashion, and which would allow for later adjustment of blood flow through a vessel. Gradual reduction in the diameter of the MPA may be desirable, but is not currently feasible with the surgical PAB approaches described above. In addition, it would be desirable to use PAB for treatment of the mature adult population suffering from left ventricle (LV) failure.

Attempts have been made to create adjustable or less invasive solutions to PAB devices. The FloWatch®-PAB device (Leman Medical Technologies SA) was designed to be surgically implanted around the exterior of the MPA in infants and uses a remote control system in order to make repeated adjustments of the level of constriction of the implanted device without additional surgical interventions.

The MPA is not a favorable location for positioning an implant due to its large diameter (~30 mm) and short length (~50 mm). The full length of the MPA is not usable for an implant due to the proximity to the pulmonary valve on one end, and the bifurcation to the pulmonary branches on the other. It is estimated that the usable length of the MPA for the implant is approximately 30 mm. Implantation of a short, wide device into the MPA is very difficult, and there is significant danger that the device will rotate or otherwise not be placed concentric with the MPA, in which case near complete blockage of the MPA could occur. In addition, the device may erroneously be placed either too close to the pulmonary valve or the bifurcation.

The apparatuses of this invention include an anchor frame that anchors the apparatus within a PA branch vessel, which then assists with the accurate positioning of a device frame that may include a medical device within the MAP. Because an apparatus of this invention is deliverable by transcatheter procedure, high risk surgery is avoided. Apparatuses of this invention may be used for treatment of CHF in adults, including LV failure. The apparatuses of this invention may remain in place for an extended time period and may adjustably control the constriction of the MPA for the duration of a therapeutic treatment.

SUMMARY OF THE INVENTION

In one embodiment, this invention provides an apparatus comprising: (a) an anchor frame for placement in a branch pulmonary artery; (b) a device frame for placement in the main pulmonary artery (MPA); and (c) a connecting section; wherein the anchor frame, the device frame and the connecting section comprise a single entity, an apparatus frame, wherein the anchor frame comprises one section of the apparatus frame, the device frame comprises another section of the apparatus frame, and the connecting section connects the anchor frame and the device frame of the apparatus frame, and wherein the anchor frame is used to position the device frame within the MPA when the apparatus is in an expanded position.

In one embodiment an anchor frame is placed in the left pulmonary artery. In one embodiment, an anchor frame further comprises a protrusion which extends into the right pulmonary artery when the apparatus is in an expanded position.

In another embodiment, an anchor frame is placed in the right pulmonary artery.

In one embodiment, an anchor section, or a connecting section or a device section, or any combination thereof of an apparatus frame of this invention comprises a zig-zag format, a stent-like format, an open-weave format, a lattice format, radially arranged strands, a crisscross format, or at least one strut, or any combination thereof.

In one embodiment, an apparatus of this invention is deliverable in a collapsed configuration by a transcatheter procedure.

In one embodiment, a device frame of this invention further comprises a medical device. In one embodiment, a medical device may be selected from the group comprising a flow restrictor, a valve, a filter, a pacemaker, a sensor or a drug delivery platform.

In one embodiment, a flow restrictor comprises at least one inflatable balloon. In another embodiment, an at least one inflatable balloon may be at least 5 inflatable balloons. In one embodiment, an inflatable balloon comprises a toroidal shaped balloon. In another embodiment, an inflatable balloon comprises a circular balloon. In one embodiment, an at least one inflatable balloon is centered within the MPA. In another embodiment, an at least one inflatable balloon is concentric with the MPA.

In one embodiment, the inflation/deflation state of the at least one balloon is able to be adjusted for an extended time period following implantation of the apparatus in a subject. In one embodiment the inflation or deflation state of an at least one balloon allows for adjustment of the effective diameter reduction within the MPA.

In one embodiment, an effective diameter reduction comprises a range of about 0% to about 100% compared with the MPA without an implanted device, wherein 0% comprises a fully open state and 100% comprises a fully closed state, wherein a percent greater than 0% and less than 100% comprises a partially open state. In one embodiment, an effective diameter reduction comprises a range of about 10% to about 90%, or 10%-30%, or 30%-70%, or 30%-60%, or 40%-70%, or 50%-60% compared with the MPA without an implanted device.

In one embodiment, an apparatus frame of this invention is self-expanding. In another embodiment, an apparatus frame of this invention is balloon expandable. In another embodiment, an apparatus frame of this invention is self-expanding and balloon expandable.

In one embodiment, this invention provides an apparatus for use in a patient with congestive heart failure. In one embodiment, a patient has left ventricular failure and preserved right ventricular function. In one embodiment, a patient is a human. In one embodiment, a patient is an infant, a child or an adult.

In one embodiment, an apparatus of this invention may be used to treat, reduce the severity of, delay the onset of, or reduce symptoms associated with any cardiac or pulmonary condition that requires blood flow reduction through a pulmonary artery. In one embodiment, a method of this invention may be used to treat, reduce the severity of, delay the onset of or reduce symptoms associated with any cardiac or pulmonary condition that requires blood flow reduction through a pulmonary artery.

In one embodiment, this invention provides an apparatus comprising: (a) an anchor frame for placement in the left pulmonary artery; (b) a device frame for placement in the main pulmonary artery (MPA); and (c) a connecting section, together the anchor frame, the connecting section and the device frame comprise a single entity, an apparatus frame, wherein the anchor frame comprises one section of the apparatus frame and the device frame comprises another section of the apparatus frame, and the connecting section connects the anchor frame and the device frame of the apparatus frame, and wherein the apparatus frame comprises Nitinol shape-memory alloy and is self-expanding, wherein the device frame comprises a flow restrictor device preassembled onto the device frame, and wherein the anchor frame is used to position and anchor the device frame within the MPA. In one embodiment a flow restrictor comprises a toroidal shaped balloon, wherein inflation of the balloon is adjustable and controls the effective diameter reduction of the main pulmonary artery (MPA) during treatment of a congestive heart failure patient with left ventricular failure and preserved right ventricular function. In another embodiment, a flow restrictor comprises an at least one balloon, wherein the balloon comprises a circular balloon centered within the main pulmonary artery (MPA), wherein inflation of the balloon is adjustable and controls the effective diameter reduction of MPA during treatment of a congestive heart failure patient with left ventricular failure and preserved right ventricular function. In one embodiment a flow restrictor comprises a toroidal shaped balloon, wherein said toroidal shaped balloon is concentric with the MPA, wherein inflation of the balloon is adjustable and controls the effective diameter reduction of the main pulmonary artery (MPA) during treatment of a congestive heart failure patient with left ventricular failure and preserved right ventricular function. In another embodiment, a flow restrictor comprises an at least one balloon, wherein the balloon comprises a circular balloon concentric within the main pulmonary artery (MPA), wherein inflation of the balloon is adjustable and controls the effective diameter reduction of MPA during treatment of a congestive heart failure patient with left ventricular failure and preserved right ventricular function. In yet another embodiment, a flow restrictor comprises more than one balloon, wherein inflation of the balloons is adjustable and controls the effective diameter reduction of the main pulmonary artery (MPA) during treatment of a congestive heart failure patient with left ventricular failure and preserved right ventricular function.

In one embodiment, this invention provides a method of treating, reducing the severity of, delaying the onset of or reducing symptoms associated with left ventricular failure in a human comprising implanting an apparatus of this invention comprising (a) an anchor frame for placement in a branch pulmonary artery; (b) a device frame for placement in the main pulmonary artery (MPA); and (c) a connecting section; wherein the anchor frame, the device frame and the connecting section comprise a single entity, an apparatus frame, wherein the anchor frame comprises one section of the apparatus frame, the device frame comprises another section of apparatus frame, and the connecting section connects the anchor frame and the device frame of the apparatus frame, and wherein the anchor frame is used to position the device frame within the MPA when the apparatus is in an expanded position; wherein the device frame comprises an adjustable flow restrictor; the method comprising the steps of: implanting the apparatus using transcatheter delivery such that the anchor frame resides within a branch pulmonary artery and the device frame resides within the MPA; adjusting the flow restrictor to reduce the effective diameter of the MPA; wherein implantation of the apparatus treats, reduces the severity of, delays the onset of, or reduces symptoms associated with left ventricular failure in a human.

In one embodiment, in a method of this invention, an anchor frame is placed in the left pulmonary artery. In one embodiment, an anchor frame further comprises a protrusion which extends into the right pulmonary artery when the apparatus is in an expanded position.

In another embodiment, in a method of this invention an anchor frame is placed in the right pulmonary artery.

In one embodiment, a method of this invention comprises an apparatus frame wherein an anchor frame, or a connecting section, or a device frame, or any combination thereof, comprise a zig-zag format, a stent-like format, an open-weave format, a lattice format, radially arranged strands, a crisscross format, or at least one strut, or any combination thereof.

In one embodiment, in a method of this invention a transcatheter delivery is performed with the apparatus in a collapsed configuration.

In one embodiment, in a method of this invention, an adjustable flow restrictor comprises at least one inflatable balloon. In another embodiment, at least one inflatable balloon comprises at least 5 inflatable balloons. In one embodiment an at least one inflatable balloon comprises a toroidal shaped balloon. In another embodiment, an at least one inflatable balloon comprises a circular balloon.

In one embodiment, a method of this invention comprises centering the at least one inflatable balloon within the MPA.

In one embodiment, a method of this invention comprises an at least one inflatable balloon wherein the inflation/deflation state of the at least one balloon is able to be adjusted for an extended time period following implantation of the apparatus in the human adult. In one embodiment, the inflation or deflation state of the at least one balloon allows for adjustment of the effective diameter reduction within the MPA.

In one embodiment, a method of this invention comprises an effective diameter reduction of the MPA, comprises a range of about 0% to about 100% compared with the MPA without an implanted device, wherein 0% comprises a fully open state and 100% comprises a fully closed state, wherein a percent greater than 0% and less than 100% comprises a partially open state. In one embodiment, an effective diameter reduction comprises a range of about 10% to about 90% compared with the MPA without an implanted device. In one embodiment, an effective diameter reduction comprises a range of about 10% to about 30% compared with the MPA without an implanted device. In one embodiment, an effective diameter reduction comprises a range of about 30% to about 70% compared with the MPA without an implanted device. In another embodiment, an effective diameter reduction comprises a range of about 30% to about 60% compared with the MPA without an implanted device. In yet another embodiment, effective diameter reduction comprises a range of about 40% to about 70% compared with the MPA without an implanted device. In one embodiment, an effective diameter reduction comprises a range of about 50% to about 60% compared with the MPA without an implanted device.

In one embodiment a method of this invention further comprises the step of adjusting step-wise the inflation state of the at least one balloon. In one embodiment, an at least one balloon is connected to an inflation tube. In one embodiment, a method of this invention further comprises attaching the proximal end of the inflation tube to a subcutaneously implanted port after implantation of the apparatus. In one embodiment, a method of this invention further comprises injecting or withdrawing a fluid through the port resulting in inflation and/or deflation of the at least one balloon. In one embodiment, a fluid is a saline solution.

In one embodiment of a method of this invention, an adjustable flow restrictor is preassembled and attached to the device frame prior to apparatus implantation. In one embodiment, an apparatus frame is self-expanding. In one embodiment, an apparatus frame is balloon expandable. In another embodiment, an apparatus frame of this invention is self-expanding and balloon expandable.

In one embodiment, a method of this invention is for use with a human infant, a human child or a human adult.

In one embodiment, this invention provides a method of repositioning, supporting or repositioning and supporting the interventricular septum in a LV failure patient comprising implanting an apparatus comprising: (a) an anchor frame for placement in a branch pulmonary artery; (b) a device frame for placement in the main pulmonary artery (MPA); and (c) a connecting section; wherein the anchor frame, the device frame and the connecting section comprise a single entity, an apparatus frame, wherein the anchor frame comprises one section of the apparatus frame, the device frame comprises another section of apparatus frame, and the connecting section connects the anchor frame and the device frame of the apparatus frame, and wherein the anchor frame is used to position the device frame within the MPA when the apparatus is in an expanded position; wherein the device frame comprises an adjustable flow restrictor; the method comprising the steps of: implanting the apparatus using transcatheter delivery such that the anchor frame resides within a branch pulmonary artery and the device frame resides within the MPA; adjusting the flow restrictor to reduce the effective diameter of the MPA; wherein implantation of the apparatus in a human repositions, supports or repositions and supports the interventricular septum in a LV failure patient.

In one embodiment, this invention provides a method of treating, reducing the severity of, delaying the onset of or reducing symptoms associated with left ventricle failure in an adult subject, said method comprising pulmonary artery banding (PAB). In another embodiment, PAB comprises external PAB. In another embodiment, PAB comprises intravascular PAB.

BRIEF DESCRIPTION OF THE SEVERAL VIEWS OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A shows a heart having normal physiology. FIG. 1B illustrates a heart with acute left ventricle (LV) distension, wherein the interventricular septum has deflected into the right ventricle.

FIG. 4A depicts an anchor frame having a stent-like, or crisscross strand, format connected with a connecting section, in this embodiment including multiple struts arranged longitudinally, further connected to a device frame having a different stent-like, or zig-zag strand, format. In this embodiment, the anchor frame has been implanted in the LPA, and the connecting frame extends through the bifurcation connecting with the device frame in the MPA. The connecting section, in one embodiment, may accommodate the not completely linear geometry required of an apparatus frame in order to connect an anchor frame in the LPA with a device frame in the MPA. In this embodiment, placement of the anchor frame in the LPA anchors and positions the device frame in the MPA. FIG. 4B depict another embodiment, wherein the anchor frame includes a non-symmetric protrusion residing in the RPA to prevent downstream movement of the apparatus. In this figure, only a single strut is depicted in the connecting section, although the connecting section can be made up of more struts, a stent-like section, or other formats of a connecting structure. FIG. 4C depicts an apparatus frame having hooks to hook into the surrounding vascular wall. Hooks are shown on both the anchor frame and the device frame. In some embodiments, hooks may be present only on the anchor frame, only on the device frame, or on both the anchor frame and the device frame. FIG. 4D depicts an anchor frame having a stent-like configuration connected with a connecting section, shown as including a single strut arranged in a mild arc but in general including other struts or other connecting structure, to a device frame having a stent-like configuration. In this embodiment, the anchor frame has been implanted in the RPA, and the connecting frame extends along the RPA connecting with the device frame in the MPA. In this embodiment, placement of the anchor frame in the RPA positions the device frame in the MPA. FIG. 4E depicts an apparatus frame wherein a circular balloon, which may in one embodiment be tapered at one end as shown here, wherein said balloon is tapered in the direction of flow, has been attached to the anchor frame by struts protruding from the anchor frame. The struts function to keep the balloon centered concentrically in the MPA. FIG. 4F depicts an apparatus frame wherein a circular balloon has been attached to both the anchor frame and the device frame by struts protruding from both of these frames. The struts function to ensure that the balloon remains centered concentrically in the MPA. FIG. 4G depicts a toroidal balloon attached to the device frame such that the constriction balloon inflates from the inner vessel wall inwards towards the center line of the MPA. As seen in FIG. 4G, in one embodiment, the cross-section of the toroidal balloon is circular, and in another embodiment, the cross-section of the toroidal balloon is semi-circular (not shown). FIG. 4H depicts an apparatus frame showing a toroidal balloon connected to the device frame, with the balloon, wherein the cross-section of the toroidal balloon is not circular, but has a more oblong shape. Thus, the balloon has a specific profile that may, for example, cause a force vector outward towards the wall of the artery, and function to keep the balloon secure against the sides of the MPA vessel.

As shown in FIG. 5A, in one embodiment, the toroidal balloon is partially inflated such that the effective diameter of the MPA in the area of the balloon is smaller than the original diameter of the MPA. As depicted in the embodiment of FIG. 5A, the cross-sectional shape of the balloon is approximately a semi-circle. FIG. 5B shows an embodiment wherein the toroidal balloon is completely deflated, a state corresponding, for example, to after completion of treatment in which the fluid in the balloon is completely removed. An inflation tube is shown attached to the balloon in FIGS. 5A and 5B, and descends along a vessel wall of the MPA towards the pulmonary valve. The tube may travel through the right side of the heart and through a wall of an upstream vein at which point it can be attached on its other end (proximal end) to a subcutaneously implanted inflation port to allow for control of degree of inflation of the toroidal balloon (port not shown). As used herein, the term "proximal end" refers in one embodiment to the end, for example of an inflation tube, closest to the inflation port. As used herein, the term, "distal end" refers in one embodiment to the end, for example of an inflation tube, furthest from the inflation port, and in one embodiment, connected to the flow restriction balloon.

FIG. 5C shows an embodiment with the balloon in an inflated state, thereby significantly reducing the effective diameter of the MPA and creating resistance to blood flow to the lungs. FIG. 5D shows an embodiment with the balloon slightly inflated, wherein the connecting section may be observed. FIG. 5E shows an embodiment with the balloon completely deflated, wherein the relative positions of the anchor frame, the connecting section, and the device frame of the apparatus may all be observed.

FIG. 6A is a view with half of the vessel wall removed showing an embodiment of an apparatus having five small balloons within the device frame wherein the balloons are effectively implanted around the internal circumference of the MPA. The apparatus frame is anchored by positioning the anchor frame section in the LPA, which thereby positions the device frame section in the MPA. The view shown is of an expanded apparatus frame. Thin double lumen inflation tubes are attached to each balloon. FIG. 6B is a cross-sectional view depicting an embodiment of the apparatus showing 2.5 balloons (half of the 5 balloons shown in FIG. 6A) attached to the device frame and evenly positioned around the internal circumference of the device frame. The device frame is positioned in the MPA. Each balloon has an inflation tube, which in one embodiment is a double lumen tube. One lumen of this tube can be used for inflation of the balloon, while the other lumen houses the guide wire, which could be used for removal of the balloons after termination of treatment. The inflation tube lumens can remain separate or can all be manifolded into a single inflation tube attached to a subcutaneous port (not shown). Balloons shown are in a partially inflated state. A guide wire is shown within one lumen of one inflation tube and is used for unhooking the balloon from the device frame at a device frame attachment site, in order to remove the balloons from the apparatus after treatment. FIG. 6C is a cross-sectional view of an embodiment of an apparatus showing 2.5 balloons (half of the 5 balloons of FIG. 6A) attached to the device frame and positioned evenly around the internal circumference of the device frame. The device frame is positioned in the MPA. The balloons are shown in a deflated state with each balloon having a double lumen inflation tube with a guide wire included in one lumen, which connects the balloon to the device frame of the apparatus. In one embodiment, this illustration represents an apparatus of the invention following termination of the treatment, in which the balloons have been deflated and are in the process of being removed.

FIG. 6D presents an illustration of a cross-sectional view of an embodiment of an apparatus, expanded, having an anchor frame, a connecting section, and a device frame with multiple balloons not present within the device frame. The inflation tubes, with guide wires in one of each of the double lumen tubes, are shown after the balloons have been removed following termination of therapy. The inflation tubes may remain in place after removal of the balloons, or may subsequently also be unhooked and removed from the apparatus.

FIG. 6E depicts one embodiment of an apparatus, showing the bottom view of the balloons around the internal circumference of the device frame from below the device frame. Balloons shown are in an inflated state, thereby significantly reducing the effective diameter of the MPA and creating resistance to blood flow to the lungs. Each balloon has a double lumen inflation tube, wherein one lumen is for inflation/deflation and one lumen contains the guide wire. The inflation lumens can remain separate or can all be manifolded into a single inflation tube attached to a subcutaneous port. FIG. 6F depicts one embodiment of an apparatus, showing the bottom view of balloons around the internal circumference of the device frame from below the device frame. Balloon shown are completely deflated at the termination of treatment, prior to removal of the balloons. The double lumen inflation tube associated with each balloon has been indicated.

Figure 1A:
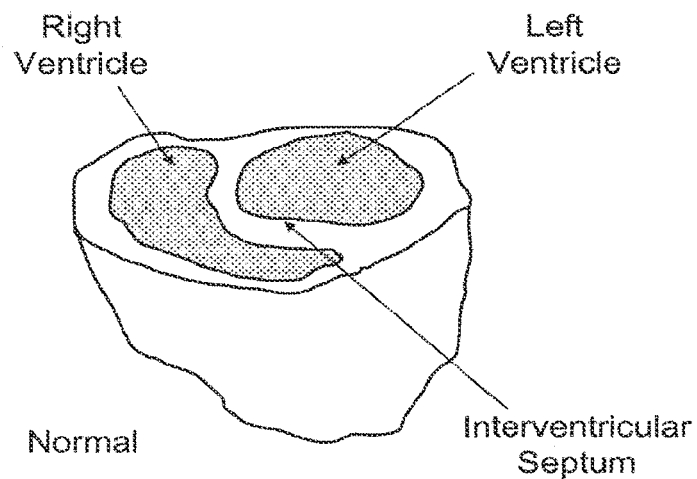
FIGS. 1A-1B depict a bird's eye internal view of the right and left ventricles of the heart and the interventricular septum positioned between these chambers.

It will be appreciated that for simplicity and clarity of illustration, elements shown in the figures have not necessarily been drawn to scale. For example, the dimensions of some of the elements may be exaggerated relative to other elements for clarity.

DESCRIPTION OF SPECIFIC EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Apparatuses

In one embodiment, an apparatus of this invention comprises (a) an anchor frame, (b) a connecting section, and (c)

a device frame, wherein the anchor frame, the connecting section and the device frame together comprise a single entity, an apparatus frame, wherein the anchor frame comprises one section of the apparatus frame and the device frame comprises another section of the apparatus frame, and the connecting section connects the anchor frame with the device frame, and the anchor frame is used to position the device frame within the main pulmonary artery (MPA). The anchor frame, connecting section and the device frame provide a platform structure, which in certain embodiments may be in a collapsed or expanded configuration.

As used throughout, the term "platform structure" refers in one embodiment to an anchor frame section, a connecting section and a device frame section of an apparatus of this invention. In some embodiments, the term "platform structure" may be referred to as an "apparatus", "apparatus frame" or "platform frame" having all the same meanings and qualities.

Figure 2:
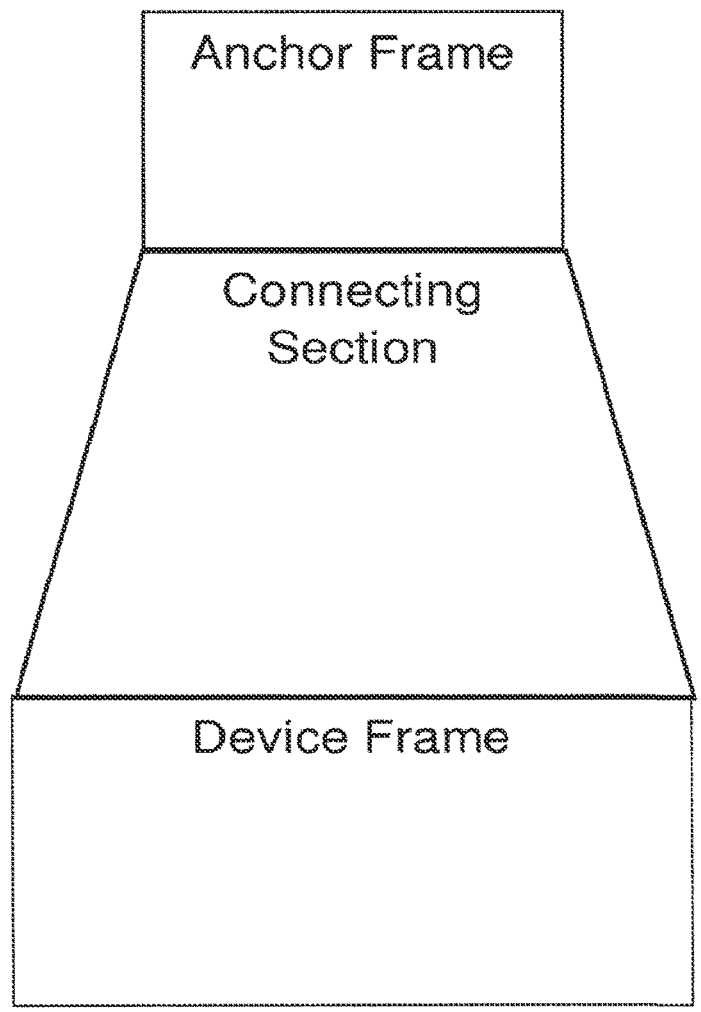
FIG. 2 presents a block diagram of one embodiment of the invention showing an apparatus frame comprising an anchor frame and a device frame with a connecting section between these two frames.

Reference is now made to FIG. 2. FIG. 2 presents an embodiment of an apparatus comprising an apparatus frame of the invention in block diagram form. The entity includes three sections, an anchor frame section, a device frame section and a connecting section that connects the anchor frame with the device frame. Placement of the anchor frame section within a branch of the pulmonary artery anchors and establishes the placement of the device frame within the MPA. In one embodiment, a connecting section of this invention can include a zig-zag format, a stent-like format, an open weave format, a mesh format, a lattice format or a crisscross format or may include at least one strut, or any combination thereof (FIG. 3 and FIGS. 4A-4H).

As used herein, the term "expanded configuration" refers in one embodiment to an apparatus frame of this invention after deployment. In one embodiment, an apparatus frame may be self-expanding following deployment. In another embodiment, an apparatus frame may be balloon expandable following deployment. In another embodiment, an apparatus frame of this invention is self-expanding and balloon expandable. In another embodiment, an apparatus frame comprises at least a portion sections that is self-expanding and at least a portion that is balloon expanding. In another embodiment, self-expanding and balloon expanding portions do not overlap. In an alternative embodiment, self-expanding and balloon expanding portions comprise some overlap. In another embodiment, overlap comprises less than about 1% of the apparatus. In another embodiment, overlap comprises less than about 5% of the apparatus. In another embodiment, overlap comprises less than about 10% of the apparatus. In another embodiment, overlap comprises less than about 20% of the apparatus. In another embodiment, overlap comprises less than about 30% of the apparatus. In another embodiment, overlap comprises less than about 40% of the apparatus. In another embodiment, overlap comprises less than about 50% of the apparatus. In another embodiment, overlap comprises less than about 60% of the apparatus. In another embodiment, overlap comprises less than about 70% of the apparatus. In another embodiment, overlap comprises less than about 80% of the apparatus. In another embodiment, overlap comprises less than about 90% of the apparatus. In another embodiment, overlap comprises about 100% of the apparatus. As used herein, the term "expanded configuration" may be used in some embodiments, interchangeably with "expanded" or "expanded apparatus" or "expanded apparatus frame" or expanded conformation" having all the same qualities and meanings.

In one embodiment, an anchor frame may be placed in the left pulmonary artery (LPA). In another embodiment, an anchor frame may be placed in the right pulmonary artery (RPA). By placing and expanding an anchor frame within a pulmonary artery branch, the device frame section of the apparatus may be accurately positioned within the MPA, ensuring concentric implantation within the MPA. In one embodiment, an anchor frame further includes a protrusion. When an apparatus of this invention is implanted such that the anchor frame is place within the LPA, in one embodiment an anchor frame protrusion extends, asymmetrically, into the RPA to prevent downstream movement of the apparatus. (FIG. 4B) Vice versa, when an apparatus of this invention is implanted such that the anchor frame is place within the RPA, in one embodiment an anchor frame protrusion extends into the left pulmonary artery to prevent downstream movement of the apparatus.

Movement of the device frame may be prevented by the placement and expansion of the anchor frame, as well as the expansion of the device frame itself. In one embodiment following deployment of an apparatus of this invention, the anchor frame is positioned and released and this positions the device frame. Future movement is prevented by the radial strength of the anchor frame and the device frame structures. In another embodiment, future movement may be prevented by the use of hooks. In yet another embodiment, future movement may be prevented by protrusion of an anchor frame into the counter-lateral branch of the PA. These embodiments to prevent movement are not exclusive and may be combined, that is, in one embodiment movement may be prevented by the radial strength of the anchor frame, the radial strength of the device frame, use of hooks associated with the anchor frame, use of hooks associated with the device frame, use of hooks associated with the anchor frame and the device frame, or by a protrusion of an anchor frame into the counter-lateral branch of the PA, or any combination thereof.

In one embodiment, sutures are not needed to prevent movement of the apparatus of this invention. In one embodiment, tissue hooks are not needed to prevent movement of an apparatus of this invention.

Figure 3:
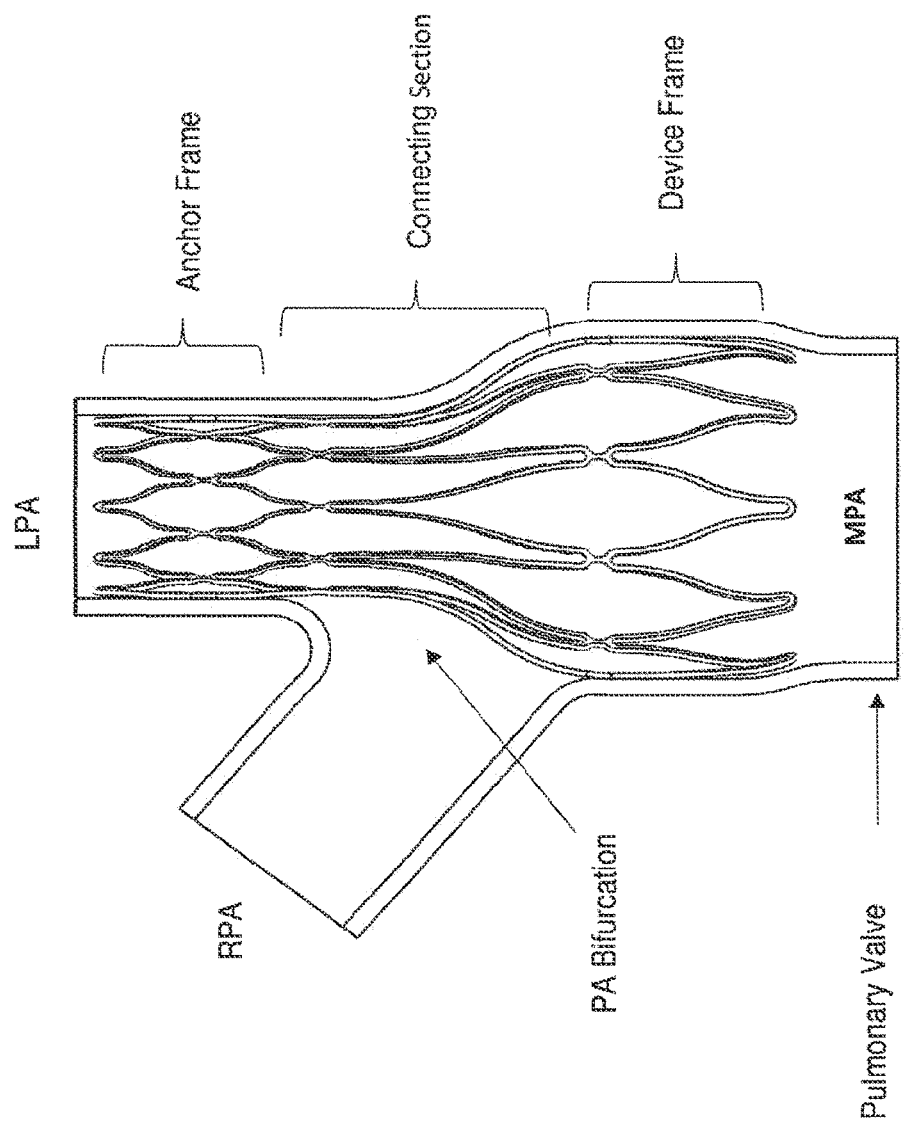
FIG. 3 presents an illustration of a cross-section of one embodiment of an apparatus frame, expanded, of this invention, showing an anchor frame section anchored within the left pulmonary artery (LPA) and a device frame section positioned in the main pulmonary artery (MPA). A connecting section serves to connect the anchor frame with the device frame in the area of the branch of the RPA. The device frame section is situated between the pulmonary valve and the PA bifurcation. As seen in the expanded configuration, the device frame may also serve to anchor the apparatus frame in place. The right pulmonary artery (RPA) is shown branching towards the left in the illustration.

Reference is now made to FIG. 3. FIG. 3 depicts, in cross-section, one embodiment of an apparatus implanted within the pulmonary artery, comprising an anchor frame section, a connecting section and a device frame section in its expanded configuration. During deployment, when the anchor frame is expanded within the LPA it exerts pressure on the inner pulmonary artery wall, thereby anchoring the anchor frame within the LPA. The positioning of the anchor frame within the LPA is chosen such that it ensures accurate placement of the device frame within the MPA, situated between the PA bifurcation and the pulmonary valve, after deployment of the connecting section and the device frame.

The size of the apparatus frame of an apparatus of this invention may be tailored to pulmonary artery dimensions present in a CHF patient, wherein the skilled artisan using knowledge of physiology of a subject could competently select the proper dimensions of an apparatus of this invention for use in a method of this invention.

Methods of measuring the internal diameter of a branch pulmonary artery and the main pulmonary artery are known in the art, such as by echocardiogram or magnetic resonance imaging (MRI). Therefore, the dimensions of an apparatus, when in an expanded configuration, may be predetermined by one skilled in the art.

In one embodiment, slight oversizing of the diameter of the platform structure, in its expanded configuration, is sufficient to retain the apparatus in place after deployment in the vessels.

In one embodiment, a device frame may have a diameter, for example in an adult human, of about ~30 mm, roughly equivalent to the maximum length that can be put into the MPA while keeping sufficiently away from the pulmonary valve or the bifurcation so as not to interfere with either. In general, use of any frame with a length to diameter ratio of less than ~2 leads to problems of stable deployment of the device. Problems may include potential for the frame to rotate and not sit concentrically within the MPA. A worst-case scenario would be for the frame to rotate or move and cause near complete obstruction of the MPA, which could require surgical intervention to correct.

In certain embodiments, this invention overcomes problems of accurate device frame positioning with the MPA, and potential for later movement from that position. In one embodiment, an apparatus frame of this invention uses an anchoring frame connected (through a connecting section) to the device frame, wherein the anchor frame is place within a branch pulmonary artery, which effectively adds length to the device frame and, may in certain instances, prevent the problem of unwanted rotation and non-concentric placement during deployment. In one embodiment, an apparatus frame of this invention may ensure concentric placement of the device frame within the MPA.

In one embodiment, wherein an apparatus of this invention is for use in a human adult, dimensions of a platform structure may, for example, comprise a length of about 55 mm (including the anchor frame, connecting section, and device frame), an expanded diameter of about 16 mm in the anchor frame (in either the LPA or RPA), and an expanded diameter of about 30 mm in the device frame (in the MPA). In another embodiment, the apparatus is sized such that the expanded anchor frame is slightly larger in diameter than the measured branch PA, and the device frame is slightly larger in diameter than the measured MPA, thereby helping to prevent movement of the expanded apparatus.

In one embodiment, an at least one inflated balloon attached to a device frame could create an effective MPA diameter of about 15 mm. In another embodiment, a partially inflated at least one balloon could create an effective MPA of less than 15 mm. In one embodiment, to create an effective MPA diameter of about 15 mm or less than 15 mm, an at least one inflated balloon may for example be a circular balloon, a toroidal shaped balloon, or multiple balloons, wherein adjustment of the inflation state of these balloons provides for an effective MPA diameter.

Reference is now made to FIGS. 4A-4H. The apparatus frames illustrated in FIGS. 4A-4H show certain embodiments of the invention. For instance, FIGS. 4A-4H show that the format structure of the strands making up an apparatus frame may differ between the anchor frame, the connecting section, and the device frame. In these embodiments, the anchor frame has been drawn with a stent-like, or crisscross pattern, format. Other embodiments may include an anchor frame with a lattice format, an open weave format, longitudinally-arranged strands, a zig-zag format, or a stent-like format. Each figure represents another embodiment of an apparatus and of how that apparatus may be implanted, such that the device frame is securely positioned within the MPA. As seen in these figures, the connecting section may be comprised of strands formed into longitudinally arranged struts. FIG. 3 and FIGS. 5A-5B and FIGS. 6A-6B show in other embodiments a connecting section having a lattice format, an open weave format, a zig-zag format, a crisscross format, or a stent-like format. In certain embodiments, as shown throughout FIGS. 4A-4H, a device frame may have a zig-zag format. In other embodiments, a device frame comprises a lattice format, an open weave format, radially arranged strands, a crisscross format, or a stent-like format.

Figure 4A:
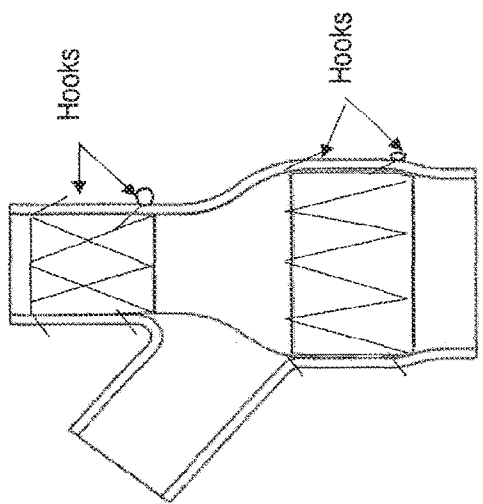
FIGS. 4A-4H present illustrations of some embodiments of an apparatus of this invention as shown in cross-section in an expanded configuration, wherein the device frame has been implanted within the MPA.
Figure 4C:
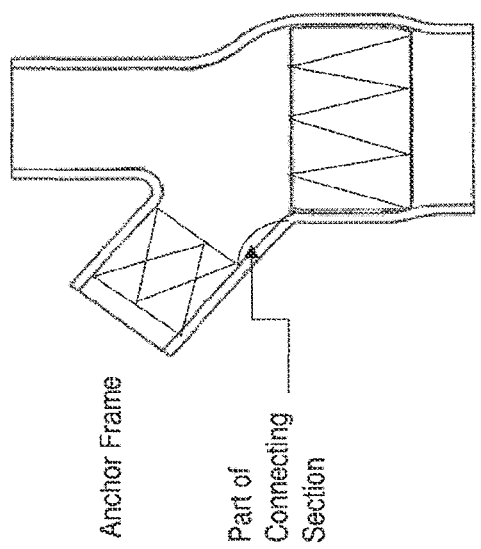

FIG. 4A shows an apparatus frame positioned with the anchor frame in the LPA and the device frame positioned in the MPA, in the absence of a medical device attached to the device frame. This could in one embodiment, represent a time prior to implantation of medical device, for example a balloon. In another embodiment, this could represent a time following termination of a therapy wherein the medical device, for example a balloon, has been removed.

Figure 4B:
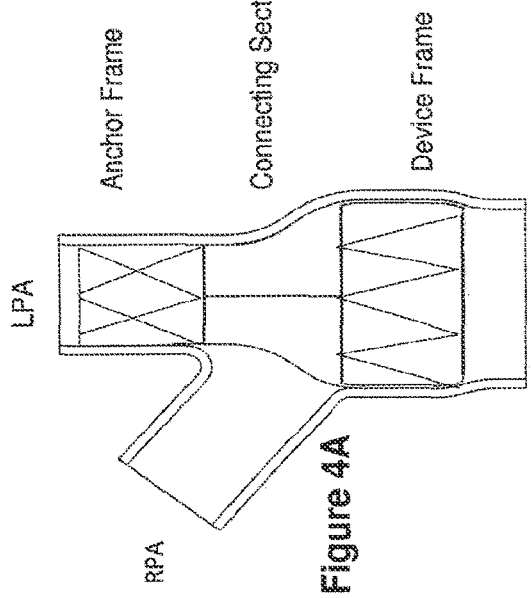

FIG. 4B shows another embodiment of an apparatus frame that includes an asymmetrical protrusion extending into the RPA to prevent downstream movement of the apparatus. If needed, an apparatus could also include hooks that penetrate the tissue of the arterial walls and secure the apparatus frame in place, as shown in one embodiment in FIG. 4C. Alternative embodiments, may include hooks only in the anchor frame or only in the device frame.

Figure 4D:
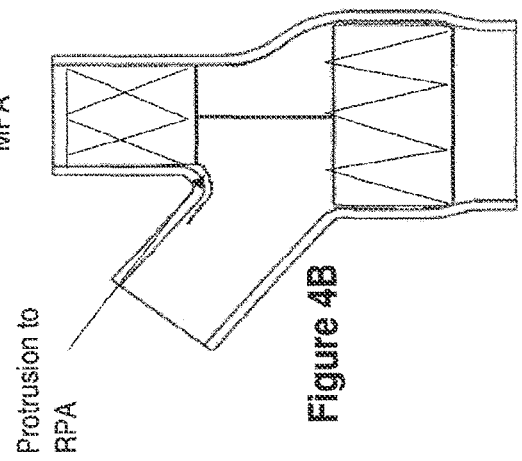

FIG. 4D illustrates an embodiment wherein the apparatus has an overall bent configuration as the anchor frame has been implanted in the RPA and is depicted with a single bowed strut, but in general may include other struts or connecting structures, attaching this anchor frame with the device frame secured within the MPA.

Figure 4E:
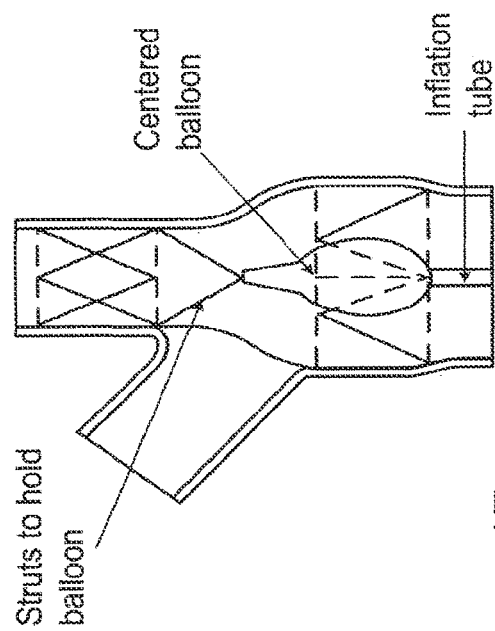

FIGS. 4E and F show embodiments of the apparatus with a circular balloon, wherein struts from the anchor frame (FIG. 4E) or from both the anchor frame and the device frame (FIG. 4F) are used to secure that the balloon in centered concentrically in the MPA. In these embodiments, the flow restrictor is positioned within the MPA such that the blood flow will be between the balloon and the walls of the MPA. Restriction of blood flow may be adjusted based on the size and shape of the balloon, which affects the flow of blood. For example, by decreasing the effective diameter of the MPA with increased inflation of a balloon, flow of blood through the MPA will be reduced.

Positioning of an apparatus of this invention comprising a flow restrictor comprising an at least one balloon affects the route of blood flowing through the MPA. Positioning of an at least one balloon may affect the path the blood takes and create directional pressures on the at least one balloon along the vascular walls. In one embodiment, an at least one balloon is centered within the MPA. In another embodiment, an at least one balloon is concentric with the MPA. In alternate embodiments, an at least one balloon is not centered within the MPA.

Figure 4G:
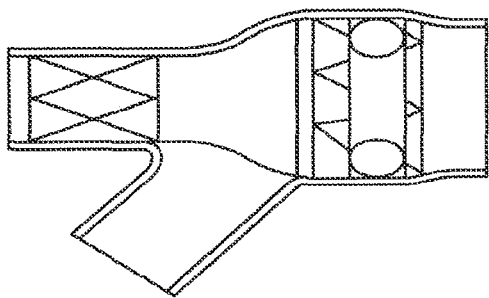
Figure 4F:
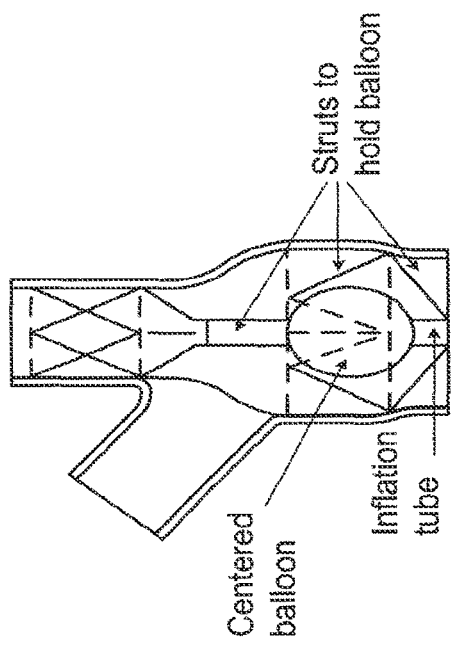
Figure 4H:
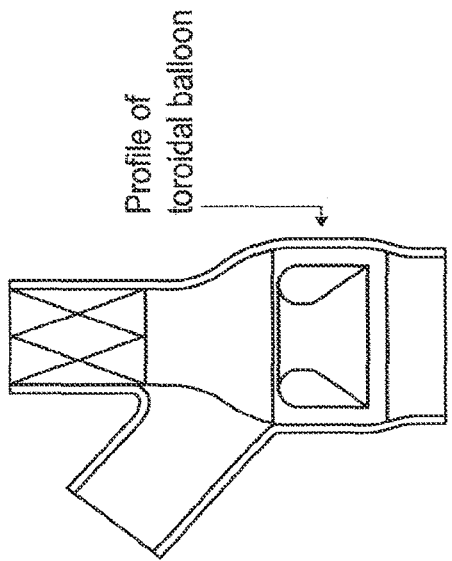
Figure 5A:
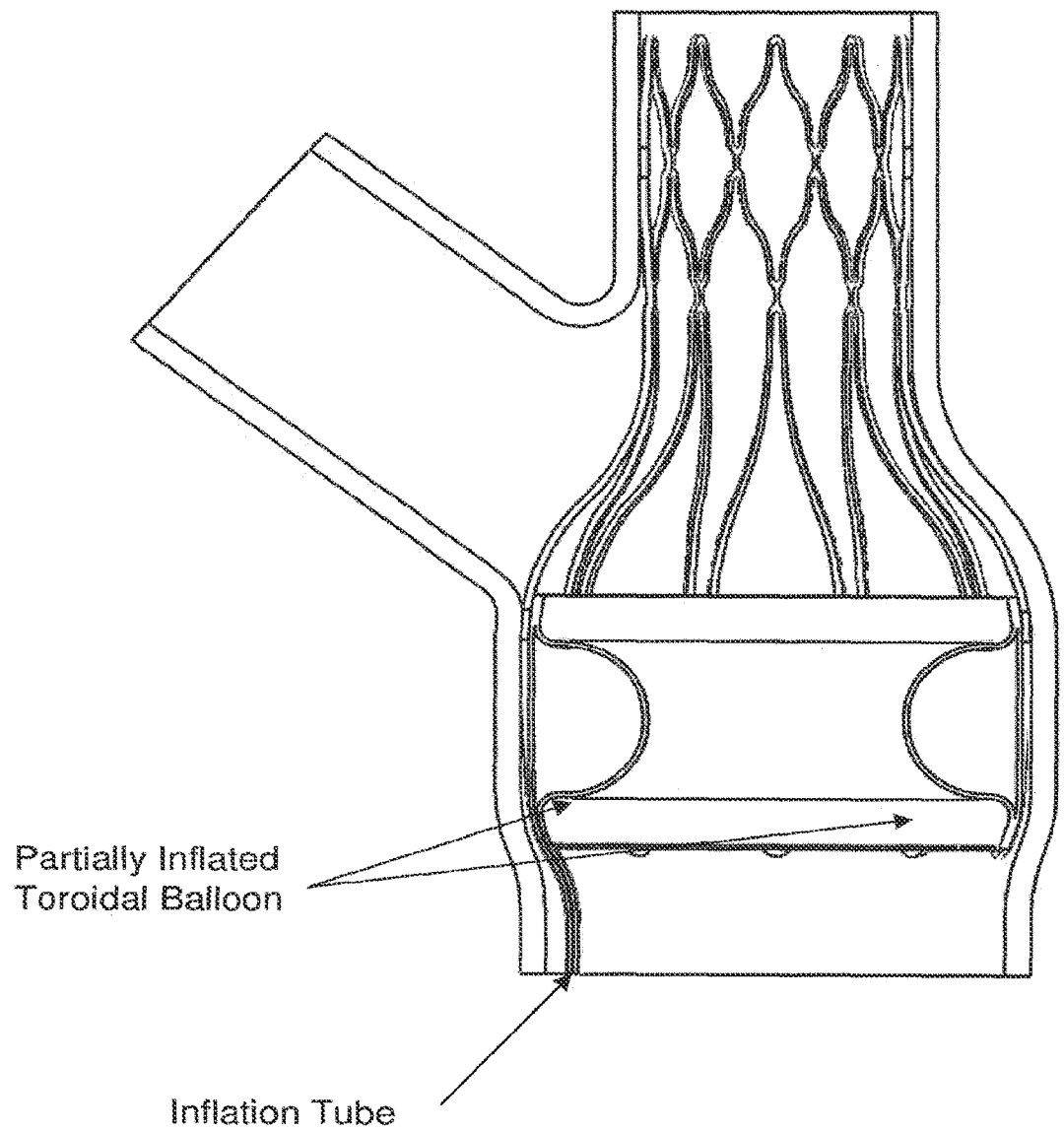
FIGS. 5A and 5B present illustrations of a cross-section of embodiments of an expanded apparatus having an anchor frame, a connecting section, and a device frame with a toroidal balloon attached to the device frame (device frame situated behind the balloon in the figure) and positioned within the MPA.

FIGS. 4G and 4H provide embodiments wherein the flow restrictor comprises a toroidal balloon positioned in the inner circumference of the MPA, wherein blood flow would be through the center opening of the balloon. FIG. 4G shows the toroidal balloon having approximately a circular cross-section, while FIG. 4H shows the toroidal balloon having a non-circular profile. In another embodiment, a toroidal balloon has an approximately semi-circular cross-section (FIG. 5A). A balloon as depicted in FIG. 4H may, for example, cause a force vector outward towards the wall of the artery, and function to keep the balloon secure against the sides of the MPA vessel.

In one embodiment, an apparatus comprising an anchor frame, a connecting section and a device frame is composed of any biocompatible material that does not interact with the blood. In one embodiment, an apparatus comprising an anchor frame, a connecting section and a device frame is composed of shape memory alloy.

As used herein, the terminology "shape memory alloy" refers to alloys which exhibit a shape memory effect. That is, the shape memory alloy may undergo a solid state phase change via molecular rearrangement to shift between a martensite phase, i.e., "martensite", and an austenite phase, i.e., "austenite". In other words, shape memory alloys are metals that "remember" their original shapes.

As is well known for minimally invasive medical procedures, the shape memory alloy may advantageously be designed to as to be stored in a deformed state (collapsed configuration) at room temperature while reverting to its predefined shape at body temperature (expanded configuration).

Shape memory alloys compatible with an apparatus of the invention may be based on various metals such as iron, copper or nickel, as long as they are biocompatible. In one embodiment, shape memory alloy is Nitinol, which is made from nickel and titanium in approximately equiatomic amounts or a slight increase of nickel. A description of Nitinol may be found, inter alia, in U.S. Pat. No. 4,425,908 whose contents are incorporated herein by reference. Small changes [less than 1%] in the percentage of nickel in the alloy confer large changes in the properties of the alloy, particularly with respect to the transformation temperature. In one embodiment, a Nitinol alloy will comprise a weight percentage of 55-56% nickel in order to have shape memory and superelastic properties at body temperature. In one embodiment, a shape memory alloy will comprise 55.1-55.6% nickel.

In one embodiment, an apparatus of this invention is in a collapsed configuration, wherein the apparatus is deliverable by a transcatheter procedure. In one embodiment, wherein the anchor frame, connecting section and the device frame of an apparatus of this invention are composed of a shape memory alloy, such as Nitinol, and the apparatus is configured to form a collapsed configuration, the apparatus is deliverable by a transcatheter procedure, and spontaneously changes to form an expanded configuration within the vessels after deployment. Such an apparatus is called a "self-expanding" apparatus.

In one embodiment, an apparatus frame or a section thereof of this invention does not comprise shape memory alloy materials. In one embodiment, an apparatus frame, or a section thereof, may be made of stainless steel. In another embodiment, an apparatus frame or a section thereof, may be made of any biocompatible metallic material. In one embodiment, an apparatus frame or section thereof is not comprised of a self-expanding material.

In an alternate embodiment, an apparatus frame or section thereof is comprised of a non-self-expanding material. In certain embodiments, wherein an apparatus frame or a section thereof is not comprised of a self-expanding material, the apparatus or sections thereof may be expanded using an at least one inflatable high-pressure balloon. In one embodiment, an apparatus frame is balloon expandable. In certain embodiments, an apparatus frame of the invention may be delivered using a transcatheter method and upon placement in the proper position expanded to an expanded configuration. In some embodiments, an apparatus frame comprised of shape memory alloy expands upon placement in a proper position. In another embodiment, an at least one high pressure balloon is used to expand an apparatus frame or sections thereof once it has been positioned.

In one embodiment, a device frame of this invention comprises a medical device. The platform formed from the anchor frame, the connecting section and the device frame supports the medical device, providing a stable platform from which it may function. The medical device may be mounted on, attached to or integrally part of the device frame. In one embodiment, an apparatus of this invention fixes the medical device in place by exerting pressure on the inner pulmonary artery walls when the anchor frame, connecting section and the device frame are in their expanded configurations.

As used herein, the term "attached" refers to one element, for example a medical device being connected or joined to something, for example, a device frame. In one embodiment, an attachment is permanent. In one embodiment, an attachment is reversible. In one embodiment, a medical device is permanently attached to a device frame. In another embodiment, a medical device is an integral part of a device frame. In yet another embodiment, a medical device may be reversibly attached to a device frame. In the case of a medical device being reversibly attached, the device may be mounted to the device frame prior to implantation, during implantation or following implantation. In one embodiment, wherein a medical device, for example a balloon, is attached to a device frame prior to delivery and implantation, the balloon would be in a deflated state and may be permanently or reversibly attached to the device frame. In one embodiment, a medical device may be un-attached from the device frame following the end of a therapeutic use of the apparatus.

In one embodiment of this invention, a medical device, for example a balloon may be attached to the device frame by being sewn onto the frame. In another embodiment, a medical device, for example a balloon may be attached by heat sealing wherein the balloon is sealed to the device frame. A medical device may be attached to the interior of a device frame using any means known in the art to be a secure attachment and to be bio-compatible for implantation in a human.

In one embodiment, a medical device is selected from the group comprising a flow restrictor, a valve, a filter, a pacemaker, a flow sensor or a drug delivery platform. In one embodiment, an apparatus of this invention comprising a medical device functions as an internal pulmonary artery band for use in the treatment of congestive heart failure (CHF).

In one embodiment, a medical device comprises a flow restrictor. In one embodiment, a medical device consists essentially of a flow restrictor. In one embodiment, a medical device consists of a flow restrictor. Placement of a flow restrictor within the MPA may, in one embodiment, decrease the effective internal diameter of the MPA. In another embodiment, placement of a flow restrictor within the MPA may increase the resistance of blood flow to the lungs. In yet another embodiment, placement of a flow restrictor within the MPA may increase the afterload of the right ventricle. In still another embodiment, placement of a flow restrictor within the MPA may increase the pressure in the right ventricle. In still another embodiment, placement of a flow restrictor within the MPA may reposition the interventrical septum to achieve a more normal physiological position. In other words, placement of the flow restrictor would correct the right-shift of the septum due to left ventricular failure. In a further embodiment, placement of a flow restrictor within the MPA may improve left ventricular function. In one embodiment, placement of a flow restrictor within the MPA may provide a combination of any and all of the effects described herein. These embodiments need not be exclusive of one another, and combinations of each may be possible.

In one embodiment, a flow restrictor comprises at least one inflatable balloon. In another embodiment, a flow restrictor comprises at least two inflatable balloons. In yet another embodiment, a flow restrictor comprises at least three, or four, or five or seven inflatable balloons. In one embodiment, a flow restrictor comprises at least five inflatable balloons. In still another embodiment, a flow restrictor comprises at least ten or more inflatable balloons.

Balloons may be inflated to form numerous pre-ordained shapes as known in the art. In one embodiment a flow restrictor comprises a toroidal shaped balloon. A toroidal balloon may, in one embodiment, has a circular cross-section. In another embodiment, a toroidal balloon has a non-circular cross section.

In another embodiment, a flow restrictor further comprises a cover. For example, in another embodiment an at least one balloon further comprises a cover. In another embodiment, a flow restrictor is a covered balloon. In some embodiments, methods of use of a covered flow restrictor device creates gradual changes in diameter, prevent eddy currents of blood around the balloons, or allows greater control over material selection for biocompatibility, hemocompatibility, etc., or any combination thereof. In certain embodiments, methods of use of a covered balloon creates gradual changes in diameter, prevent eddy currents of blood around the balloons, or allows greater control over material selection for biocompatibility, hemocompatibility, etc., or any combination thereof.

Figure 7:
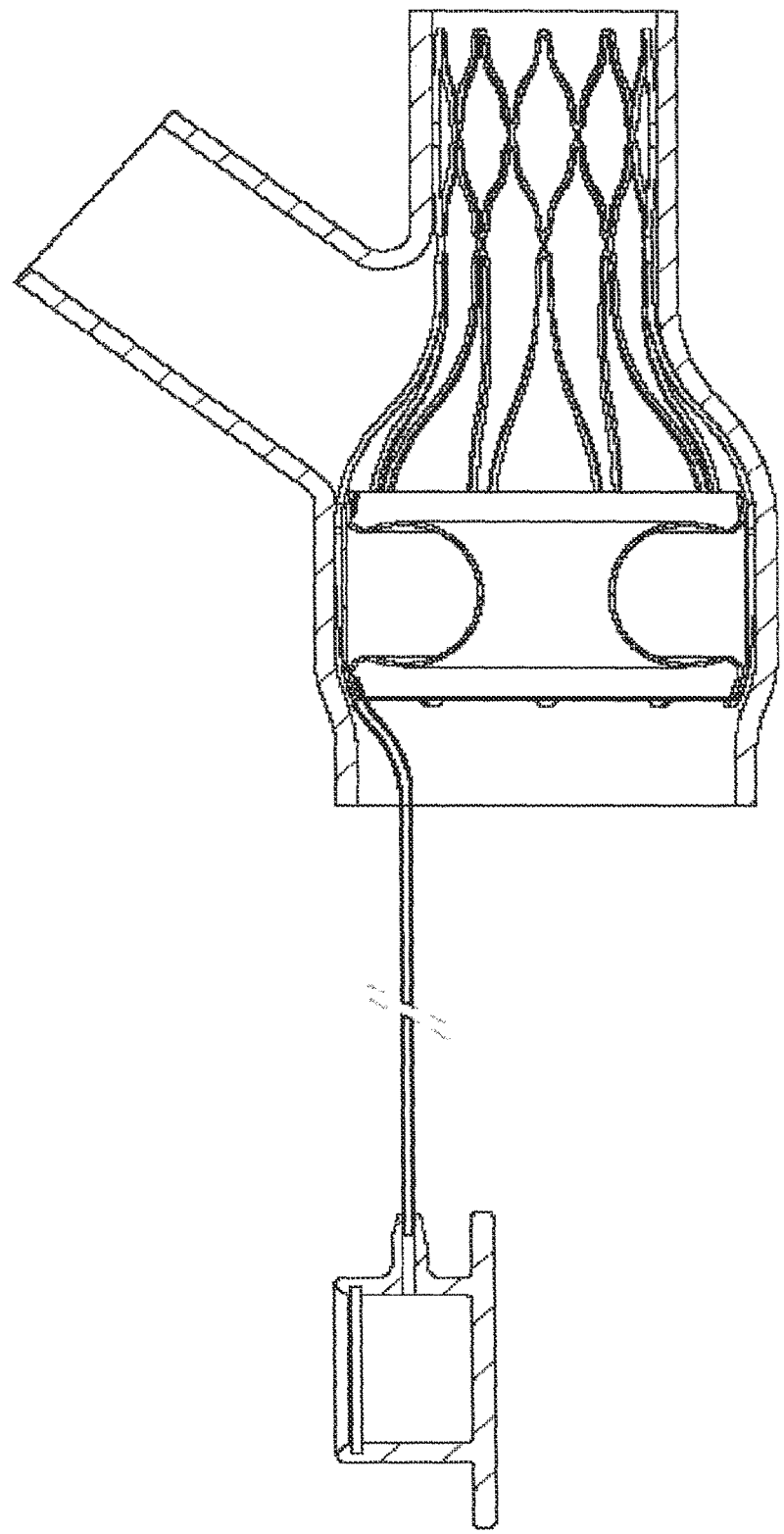
FIG. 7 presents an illustration of one embodiment of an apparatus, showing a partially inflated toroidal balloon within a device frame positioned within the MPA and anchored by an anchor frame in the LPA, wherein the balloon is attached to an inflation tube, which is further attached to a subcutaneous inflation port.

Reference is now made to FIGS. 5A-5E. FIG. 5A depicts, in cross-section, an anchor frame, a connecting section, and a device frame, in an expanded configuration wherein a toroidal balloon flow restrictor is attached on the inner circumference of the device frame. The expanded anchor frame placed in the LPA positions the toroidal balloon attached to the device frame within the MPA. Attached to the balloon is an inflation tube, wherein the distal end of the inflation tube is attached to the balloon. The inflation tube may descend along the vessel wall of the MPA, through the pulmonary valve and the right side of the heart, and through a vein feeding the right atrium. The proximal end of the inflation tube may be attached to a subcutaneously implanted inflation point to allow for control or the degree of inflation of the toroidal balloon (FIG. 7).

Figure 5B:
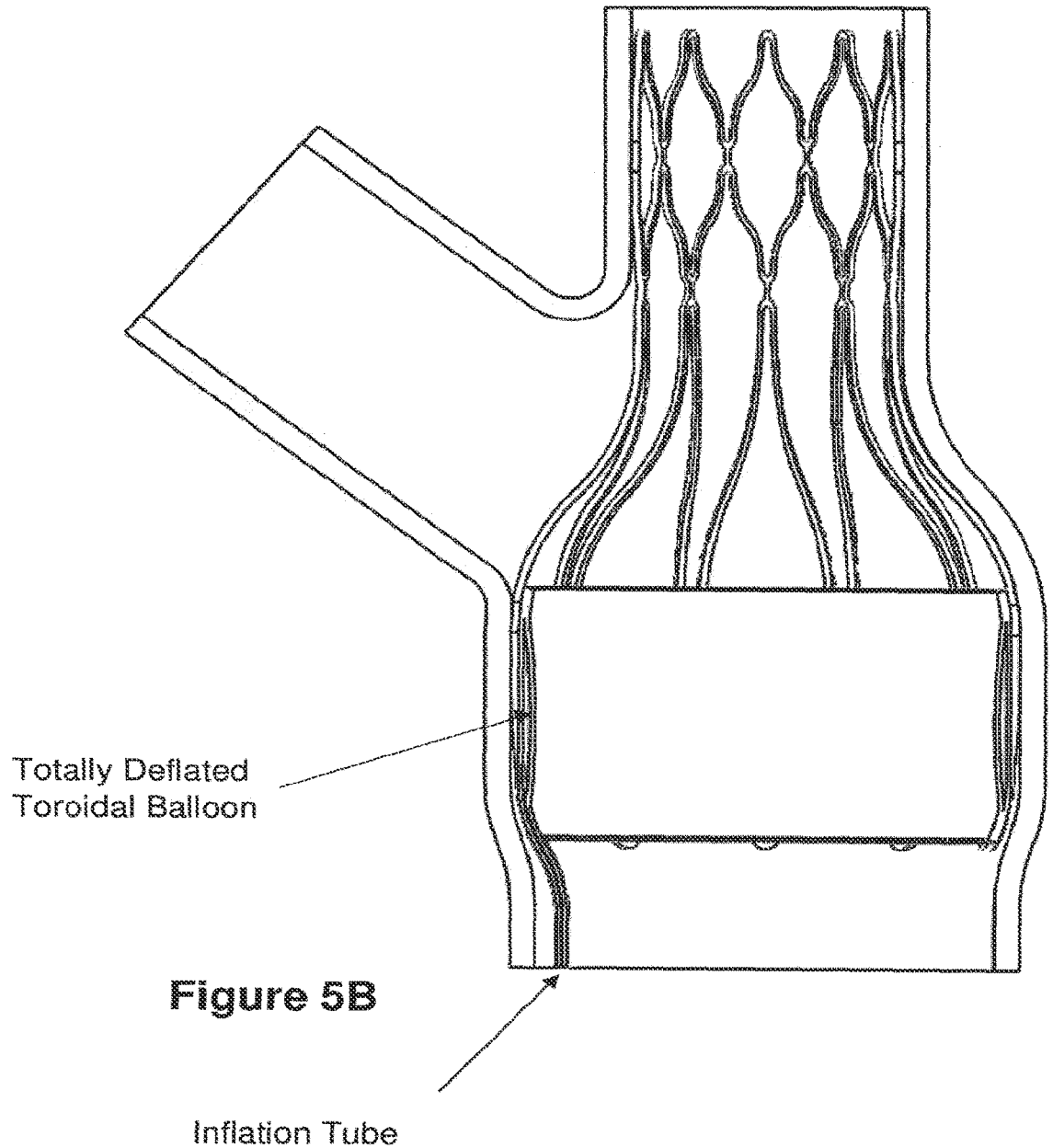

In one embodiment of this invention an inflation tube is attached to an inflatable balloon at its distal end and attached to an inflation port at its proximal end. In one embodiment, the attachment of the inflation tube to a balloon is permanent. In another embodiment, the attachment of the inflation tube to a balloon is reversible. In one embodiment, the attachment of the inflation tube to an inflation port is permanent. In another embodiment, the attachment of the inflation tube to an inflation port is reversible. The toroidal balloon illustrated in FIG. 5A has been partially inflated. FIG. 5B depicts, in cross-section, one embodiment of the invention, showing a completely deflated toroidal balloon attached to the device frame within the MPA.

In one embodiment, an inflation tube is a thin inflation tube. In some embodiments, an inflation tube of this invention comprises a hollow tube made of a polymer, which in certain embodiments is a flexible polymer with limited interference for the vessels and valves through which it is deployed. In one embodiment, an inflation tube has a single lumen. In another embodiment, an inflation tube has two lumens, one for inflation and one for use with a guide wire.

In one embodiment, an inflation tube is attached to/detached from a subcutaneously implanted inflation port by pushing/pulling the inflation tube. In another embodiment, an inflation tube is attached to/detached from an inflation port by screwing/unscrewing the inflation tube. In yet another embodiment, an inflation tube is attached to/detached from an inflation port by electrolysis or other mechanical or chemical means.

In one embodiment, an inflation port may be implanted subcutaneously within a subject concurrently with implantation of an apparatus. In another embodiment, an inflation port may be implanted within a subject prior to implantation of an apparatus. In one embodiment, an inflation port may be removed from a subject at the termination of a therapy. In another embodiment, an inflation port may be left in place at the termination of a therapy. The inflation tubes may be detached from the inflation port or may remain in place.

In one embodiment, the inflation state of an at least one balloon is adjustable. In one embodiment, adjustments may be made at the time of implantation or during a therapeutic treatment or any combination thereof. In one embodiment, adjustments may be made at the termination of a therapy, for example completely deflating an at least one balloon. In some embodiments, wherein an apparatus of this invention is left in place, it may be possible to inflate an at least one balloon at a later date dependent on the need of a subject patient. In one embodiment, adjustments to the inflation state of an at least one balloon are controlled from the inflation port by the introduction or removal of a fluid solution, for example a saline solution. In another embodiment, the at least one balloon is adjustable at any time after implantation. In yet another embodiment, the at least one balloon is adjustable only at time of implantation. In still another embodiment, the at least one balloon is not adjustable.

Figure 5C:
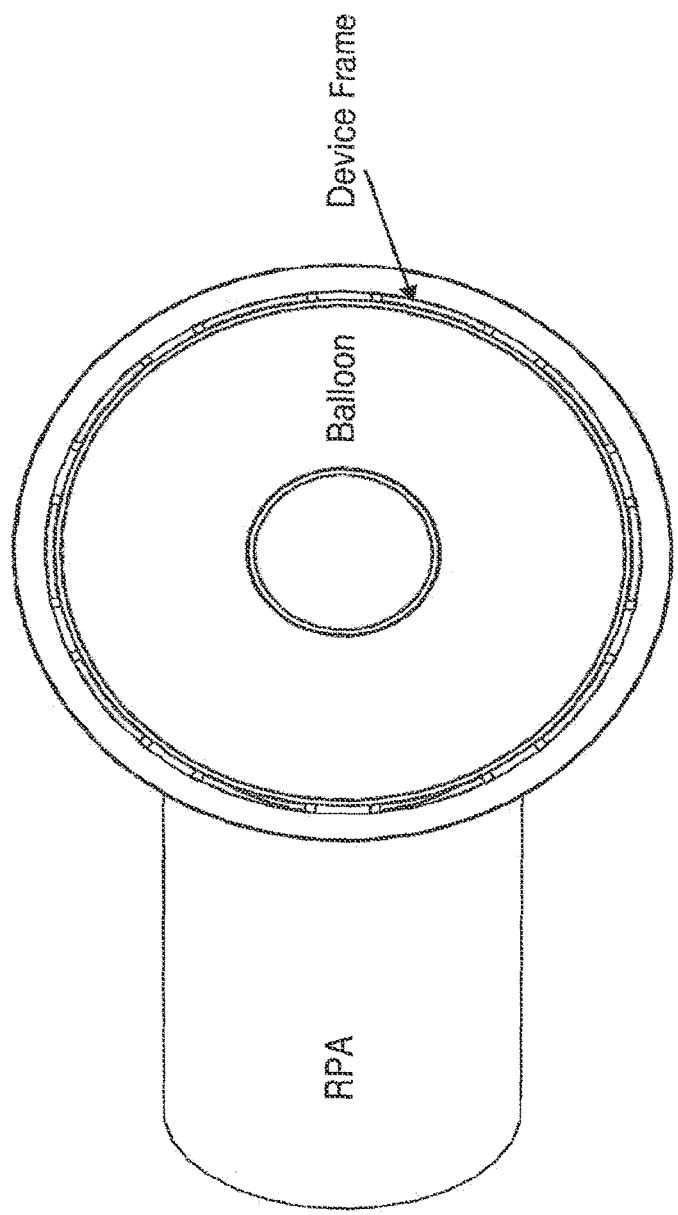
FIGS. 5C, 5D and 5E present illustrations of embodiments of an expanded apparatus of this invention implanted within the LPA and MPA, from a bottom view of FIGS. 5A and 5B, having an anchor frame, a connecting section, and a device frame with a toroidal balloon attached to the device frame and positioned within the MPA.
Figure 5D:
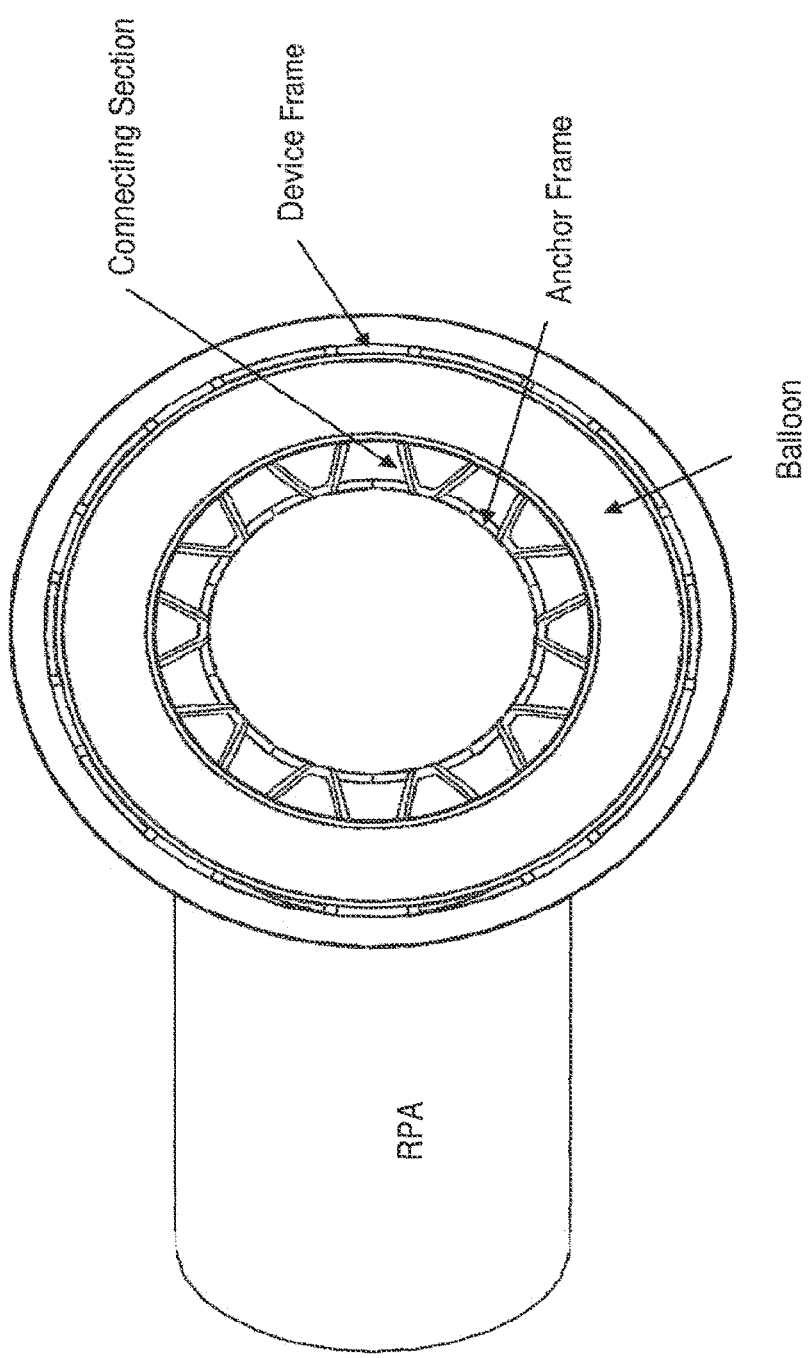
Figure 5E:
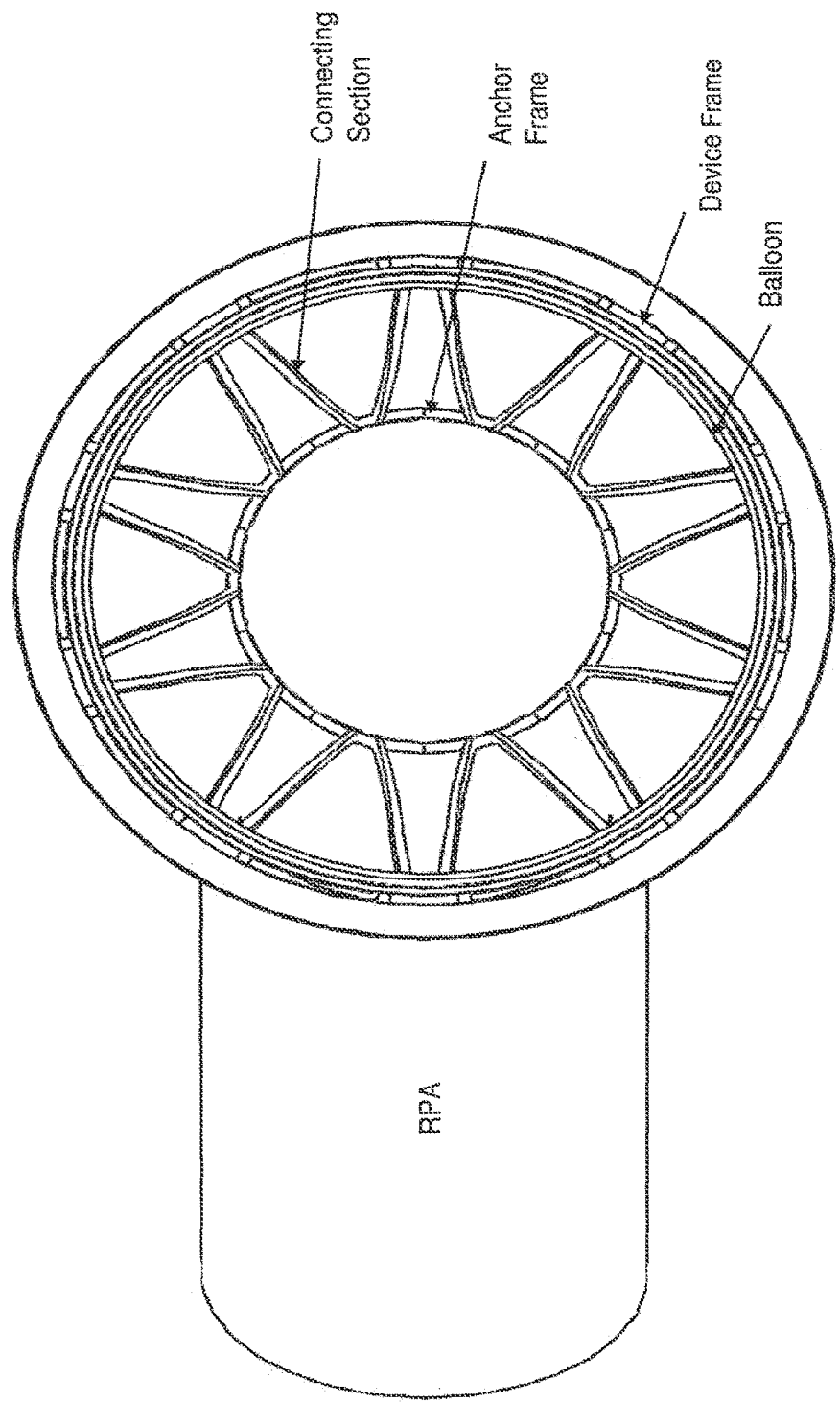

In one embodiment, inflation of a balloon may reduce the effective diameter of the MPA, creating a resistance to blood flow to the lungs. FIG. 5C depicts, in a bottom view, a partially inflated toroidal balloon attached to a device frame, from below the MPA. The effective diameter of the MPA has been significantly reduced. The anchor frame of the apparatus shown in FIG. 5C has been placed in the LPA (not observable from this angle). The device frame is observable as a thin ring and the RPA is seen extending leftward. FIG. 5D depicts, in a bottom view, an apparatus as is shown in FIG. 5C, wherein the balloon is in a less inflated state. The decreased inflation reveals the connecting section residing between the LPA and the MPA. FIG. 5E depicts, in a bottom view, an apparatus wherein the toroidal balloon has been completely deflated.

Figure 6A:
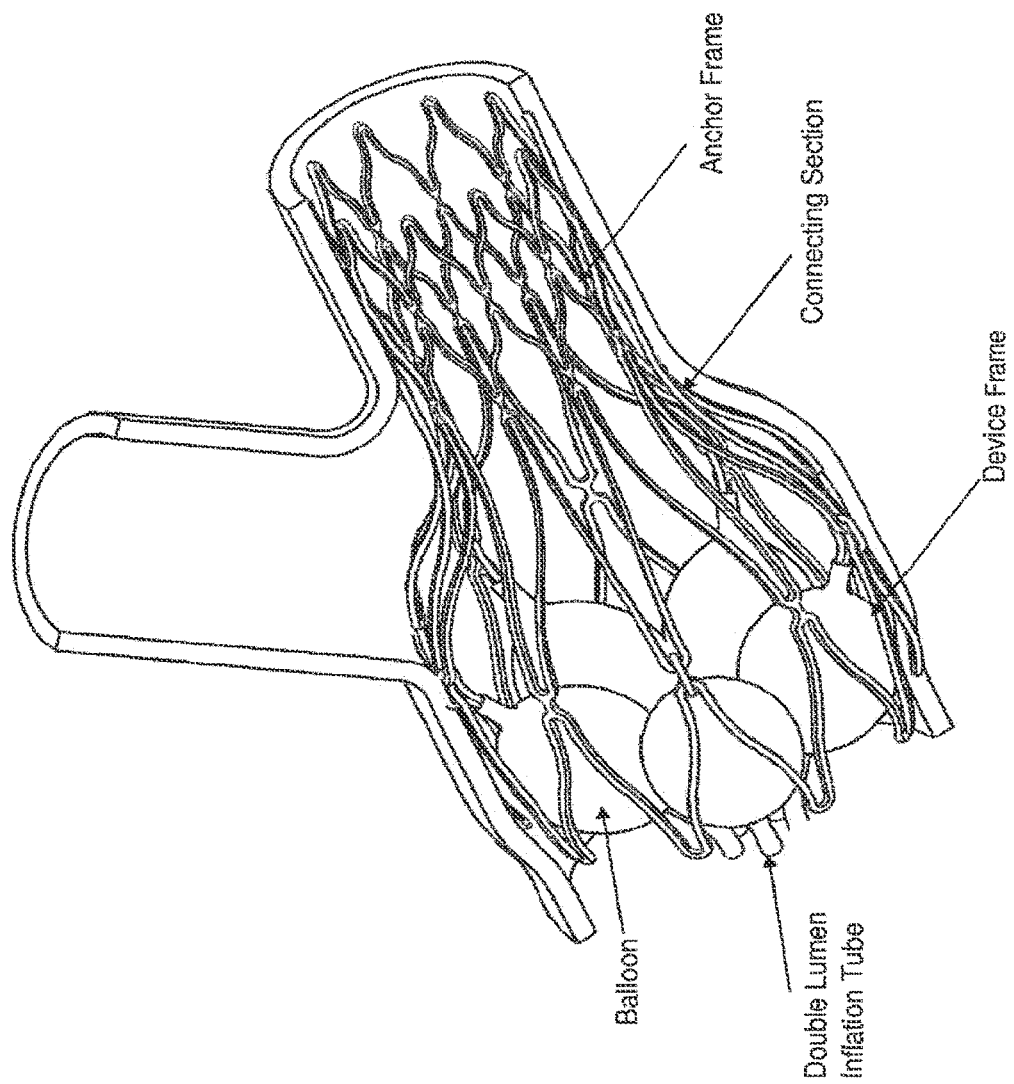
FIGS. 6A-6C present illustrations of an apparatus having an anchor frame, a connecting section, and a device frame (apparatus frame expanded and implanted within the LPA and the MPA) with multiple balloons attached to the device frame.
Figure 6B:
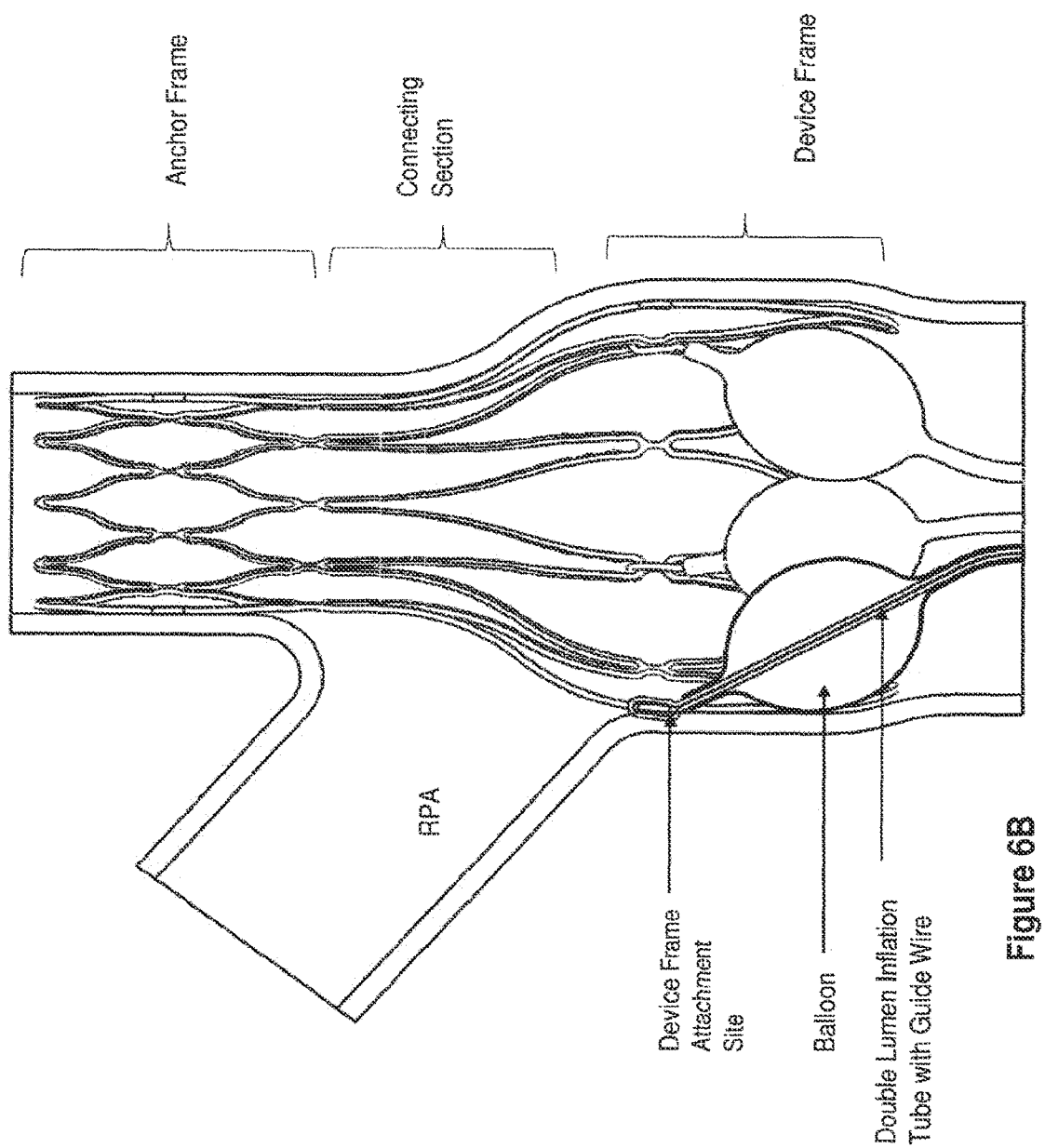
Figure 6C:
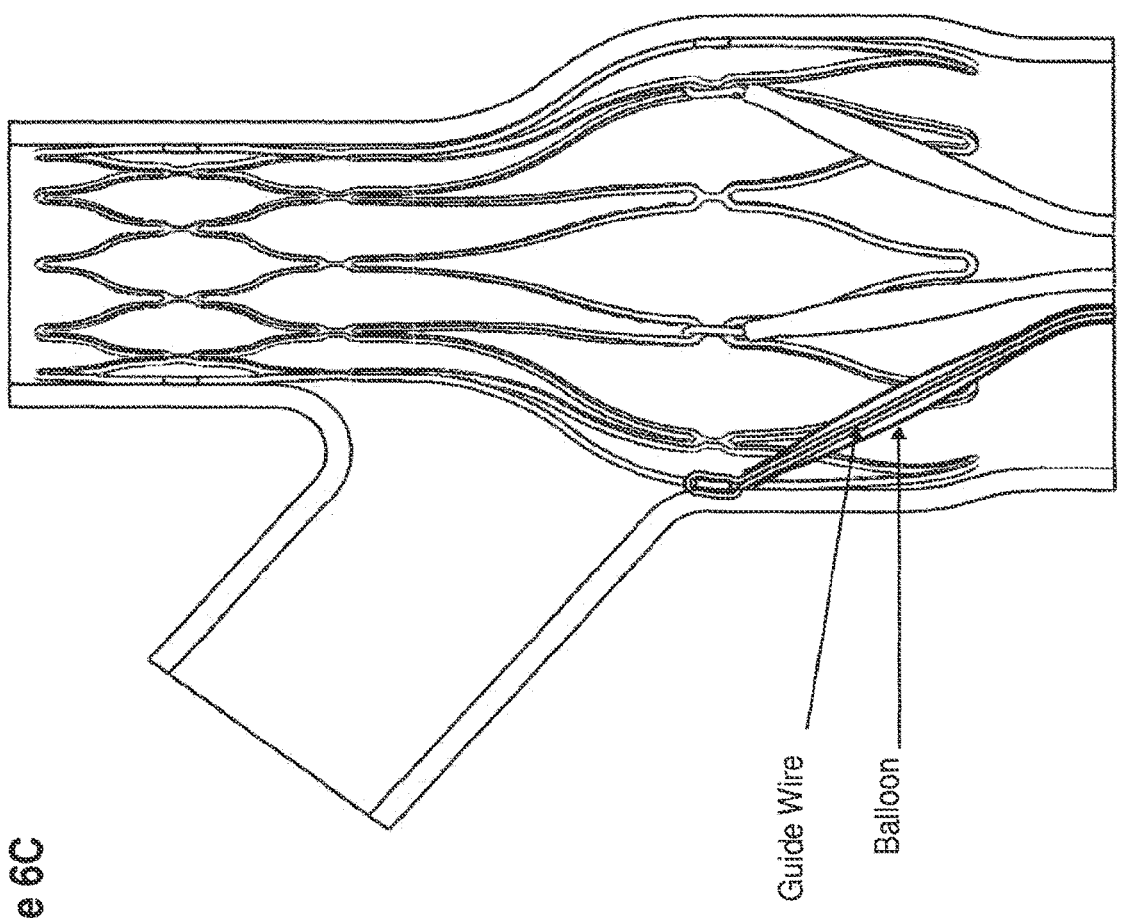
Figure 6E:
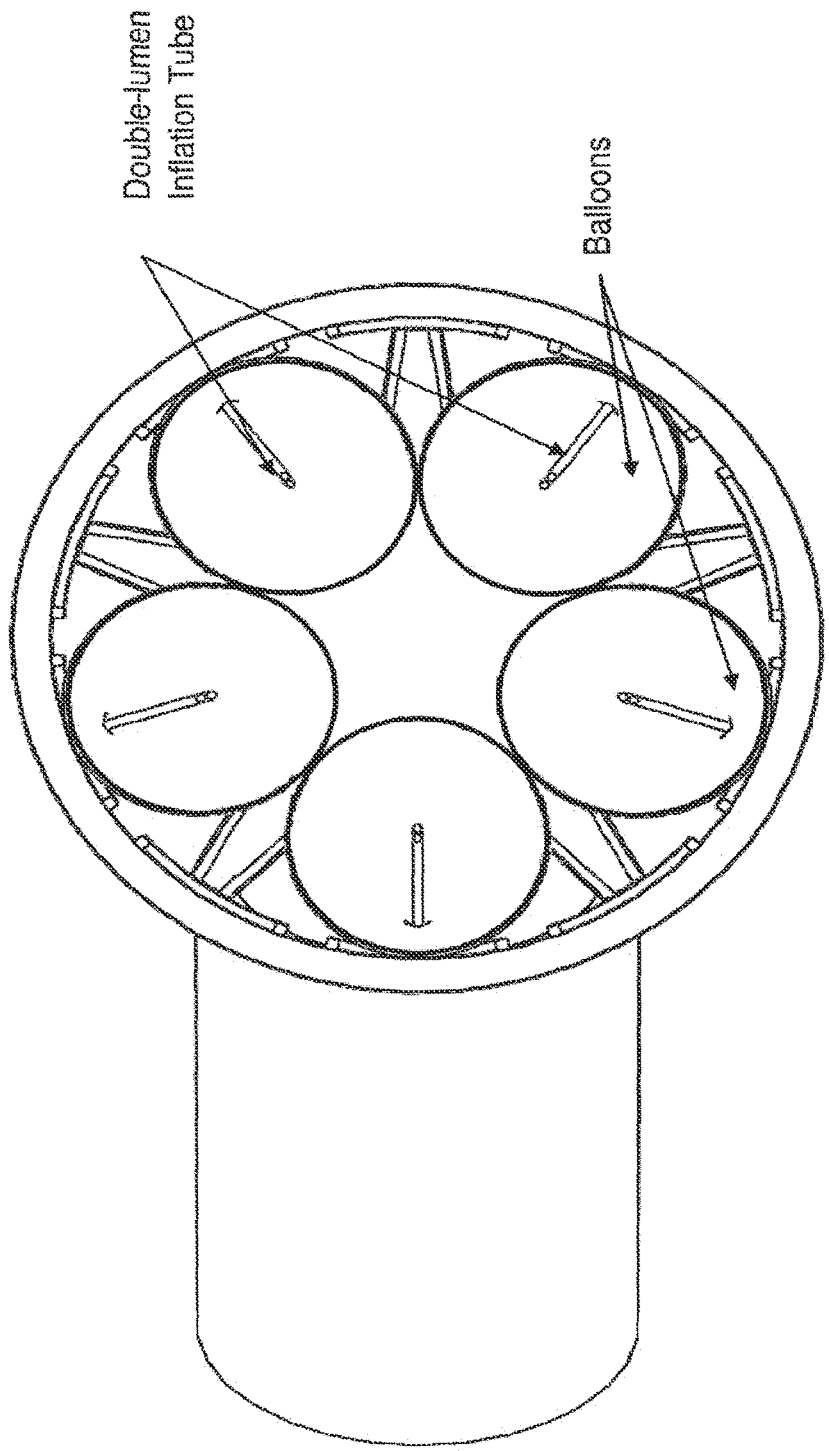
FIGS. 6E-6F present bottom view illustrations of embodiments of an expanded apparatus having an anchor frame, a connecting section, and a device frame with multiple balloons attached to the device frame, such as in FIGS. 6A and 6B.
Figure 6F:
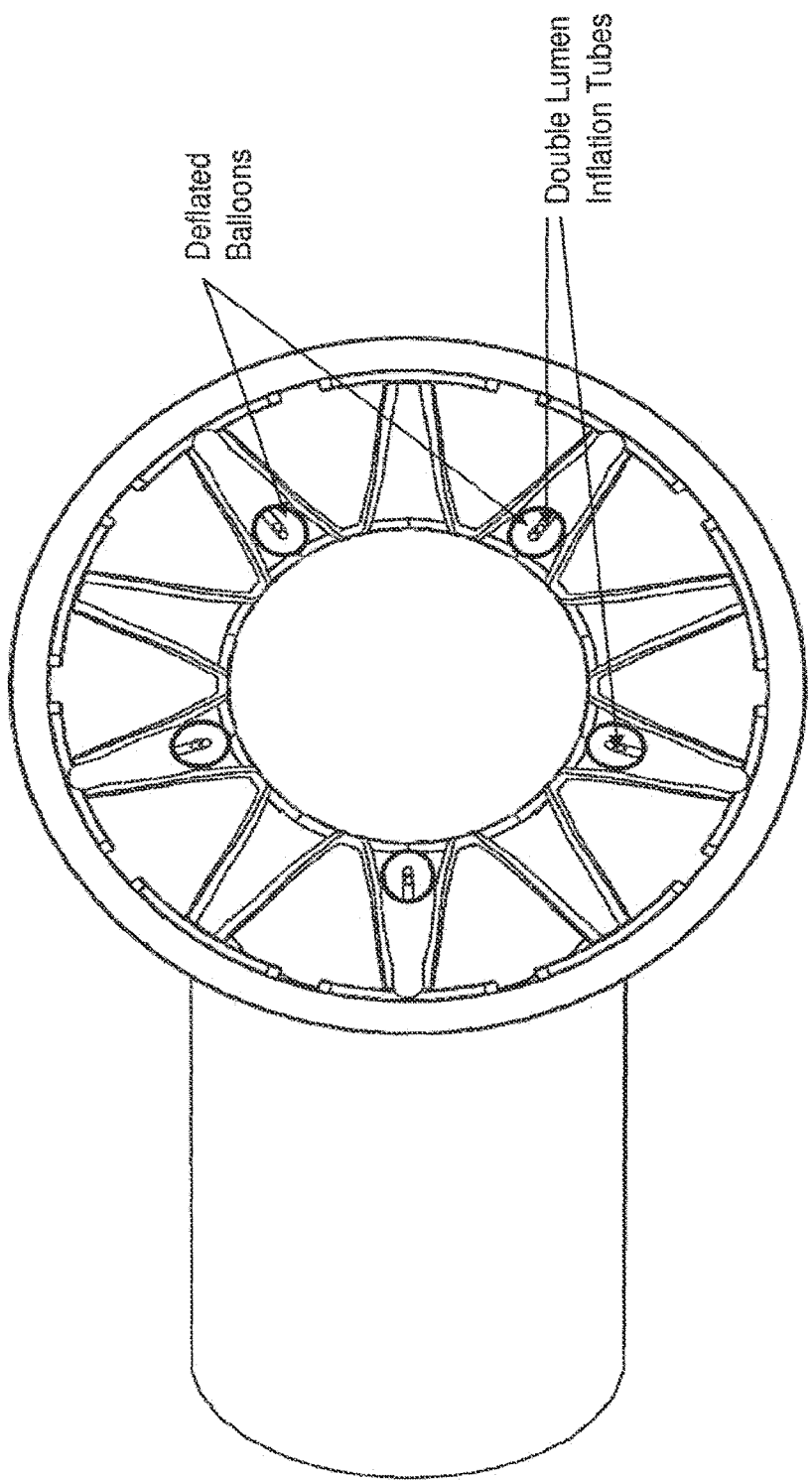

Reference is now made to FIGS. 6A 6E and 6F. FIG. 6A depicts an apparatus, wherein the anchor frame is placed in the LPA, the connecting section connects between the anchor frame and the device frame, the device frame is positioned within the MPA and five small balloons have been attached around the inner circumference of the device frame, effectively placing the five balloons in a donut-like shape within the inner circumference of the MPA (See FIG. 6E-6F). FIG. 6E shows a bottom view of an embodiment of this invention, wherein an apparatus comprises an anchor frame placed in the LPA, a connecting section connects between the anchor frame and the device frame, a device frame positioned in the MPA and having five small balloons attached to the device frame and arranged around the inner circumference of the device frame. Balloons shown are in the inflated state, thereby effectively reducing the effective diameter of the MPA and creating resistance to blood flow to the lunges. The attached double lumen inflation tubes can be seen extending from each balloon. The lattice of the connecting section can be observed between the balloons while the device frame is observable in a thin ring around the balloons.

In FIG. 6A half the vessel wall has been removed from the illustration, in order to show the arrangement of balloons. At one region of the balloons, the balloons are attached to the device frame while at another region of the balloons, the balloons are attached to inflation tubes. In another embodiment, each balloon can be attached to the device frame at more than one point on the balloon. In certain embodiments, wherein more than a single balloon is attached to a device frame, and wherein each balloon is also attached to an inflation tube, the inflation tubes may be manifolded together to form a single tube prior to attachment to an implanted subcutaneous inflation port (not shown). In this manner, balloons may be concurrently inflated or deflated. In other embodiments, wherein more than a single balloon is attached to a device frame, and wherein each balloon is also attached to an inflation tube, the inflation tubes remain separate and attach separately to subcutaneous inflation ports. In this instance, balloons may be inflated or deflated independent of one another. The attachment to the subcutaneous port may be permanent or revisable.

In one embodiment, a flow restrictor of this invention comprising multiple balloons creates a particular geometry within the MPA. A geometry created by multiple balloons may be advantageous in regulating blood flow. In one embodiment, a flow restrictor may comprise two balloons joined together end to end forming ring, similar to hot-dogs joined end to end when inflated.

In one embodiment, inflation and/or deflation of an at least one balloon of this invention comprises injecting or withdrawing a fluid through the inflation port. In one embodiment, the fluid is an isotonic saline solution. In another embodiment, a fluid is a glue. In yet another embodiment, a fluid may be beads or particles that act as a fluid. In one embodiment, regulation of inflation/deflation state of an at least one balloon is by injecting or withdrawing a fluid through the inflation port.

In one embodiment, an at least one balloon of this invention comprise a low-pressure, or compliant balloon. Compliant medical balloons are typically fabricated from polyurethane, Nylon elastomers, silicon, latex, or other thermoplastic elastomeric material. They typically have thicker wall thickness than high pressure dilatation medical balloons, and burst pressures typically range up to 2 atmospheres of pressure.

In one embodiment, the adjustable inflation of an at least one balloon provides the ability to adjust the inflation state of the balloon for an extended time period following implantation of said apparatus in a subject. In one embodiment, adjustable inflation allows for adjustment of the effective diameter within the MPA. In one embodiment, a balloon in a deflated state does not effectively reduce the diameter of the MPA. In one embodiment, wherein a flow restrictor is comprised of multiple balloons, and wherein the balloons are all in a deflated state, there is no effective reduction of the diameter of the MPA.

In one embodiment, an apparatus of this invention is adjustable, wherein an attached medical device, for example an at least one balloon may be deflated, partially inflated or fully inflated. In another embodiment, the attached medical device is adjustable at any time after implantation. In yet another embodiment, the attached medical device is adjustable only at time of implantation. In a further embodiment, the attached medical device is adjustable at the time of termination of treatment. In still another embodiment, the attached medical device is not adjustable. In another embodiment, a skilled artisan may regulate the extent to which the diameter of the MPA is reduced by partially inflating balloon(s), fully inflating balloon(s), fully deflating balloon(s), or having balloon(s) at different states of inflation.

In one embodiment, the effective reduction of the MPA diameter is directly related to the inflation state of an at least one balloon of this invention. As used herein, the phrase "effective reduction in diameter" refers to the percent reduction in diameter of the MPA in the area of the inflated balloon. For example, in an embodiment wherein a medical device is an at least one balloon and the balloon is fully deflated the effective diameter of the MPA is essentially the diameter prior to placement of an apparatus minus the thin circumference of the device frame. In other words, the effective reduction in diameter is about 0%.

In one embodiment, an effective reduction in diameter comprises a range of about 0% to about 100%, wherein 0% comprises a fully open state and 100% comprises a fully closed state, wherein a percent constriction greater than 0% and less than 100% comprises a partially open state. In one embodiment an effective reduction in diameter comprises a range of about 10% to about 90%. In another embodiment, an effective reduction in diameter comprises a range of about 40% to about 70%. In yet another embodiment, an effective reduction in diameter comprises a range of about 10% to about 20%. In still another embodiment an effective reduction in diameter comprises a range of about 20% to about 30%. In a further embodiment, an effective reduction in diameter comprises a range of about 30% to about 80%, or about 30% to about 70%, or about 40% to about 70%, or about 50% to about 70%, or about 50% to about 60%. In one embodiment, an effective reduction in diameter is about 10%, 20%, 30%, 40%, 50%, 60%, 70%, 80% or 90%.

Reference is now made to FIGS. 6B-6D. In one embodiment, a medical device is attached to a device frame of an apparatus, wherein the device frame is positioned within the MPA. In one embodiment, a balloon is attached to the device frame of an apparatus. FIG. 6B shows, in cross-section, multiple balloons partially inflated and attached to a medical device by guide wires that extend through one of the lumens of the inflation tube (not the lumen used for inflation) and through the balloon to attach the balloon to the device frame at an attachment site. In one embodiment, as shown here, the guide wires hook onto the device frame. FIG. 6C shows another embodiment of the apparatus of FIG. 6B, wherein all of the balloons are deflated. Note the presence of the guide wire within the deflated balloons. In one embodiment, guide wires threaded through a balloon and through a lumen of the inflation tube, which is not the lumen for inflation, could be attached to the device frame prior to deployment of the apparatus in the MPA. In another embodiment, guide wires threaded through a balloon and through an inflation tube (in a separate lumen than that used from inflation) could be attached to the device frame at the time of implantation or following implantation of a platform frame prior to balloon inflation. In one embodiment, the guide wires extend for the entire length of the double lumen inflation tube, and terminate at the subcutaneous inflation port, for later use in unhooking and removing the balloons after termination of treatment. In one embodiment, guide wires may be made of any biocompatible material known in the art able to secure a balloon to an apparatus frame.

Sites of attachment, for example for guide wires, may be around the circumference of the device frame, as shown in FIGS. 6B and 6C. Alternatively, a balloon could be stitched to the device frame or heat sealed to the device frame. Each balloon in FIGS. 6B and 6C has a double lumen inflation tube, the inflation lumen of which can each remain separate or they can all be manifolded into a single inflation tube attached to a subcutaneous port. FIG. 6D depicts, in cross-section, an apparatus comprising an anchor frame, a connecting section, a device frame and the attached guide wires. This illustrates, in one embodiment, an apparatus of this invention during the process of removal of balloons. Balloons may be removed from the guide wires or together with the guide wires after termination of therapy. FIG. 3 shows, in one embodiment a cross-section of an apparatus of this invention, wherein the guide wires and balloons have been removed from the device frame after termination of therapy.

In one embodiment, attachment of a guide wire is reversible. In another embodiment, attachment of a guide wire is permanent. In one embodiment, attachment of a medical device comprises guide wires. In one embodiment, attachment of a balloon device comprises guide wires.

In one embodiment, an apparatus comprising a medical device, comprising a flow restrictor, comprising an at least one balloon, comprises guide wires located within the at least one balloon.

In some embodiments, an apparatus comprises a medical device, comprising a flow restrictor, comprising at least one balloon, wherein the at least one balloon is attached to the device frame in a deflated state prior to implantation of the apparatus or at the end of a treatment therapy.

In one embodiment, a medical device is assembled onto the device during implantation, attaching the medical device to the device frame following positioning of the device frame within the MPA.

In one embodiment, a medical device is detached from the device frame and withdrawn from the implantation site at the end of a treatment therapy.

In one embodiment, an apparatus of this invention comprising an anchor frame, a connecting section and a device frame are self-expanding. In this embodiment, the apparatus is configured to form a collapsed configuration within the delivery catheter, the apparatus is deliverable by a transcatheter procedure, and spontaneously changes to form an expanded configuration within the vessels after deployment. In another embodiment, an anchor frame is self-expanding. In another embodiment, an anchor frame is balloon expandable. In another embodiment, a device frame is self-expanding. In another embodiment, a device frame is balloon expandable. In another embodiment, a connecting section is self-expanding. In another embodiment, a connecting section is balloon expandable. In another embodiment, an anchor frame is self-expanding, and a device frame is balloon expandable. In another embodiment, a device frame is self-expanding, and an anchor frame is balloon expandable.

In one embodiment, an anchor frame, a connecting section and the device frame are balloon expandable. In one embodiment, the apparatus is configured to form a collapsed configuration within the delivery catheter, the apparatus is deliverable by a transcatheter procedure, the apparatus is positioned at the desired location in the vessels, and a high-pressure balloon is then used to expand the apparatus to form its final expanded configuration within the vessels. In certain embodiments, comprising use of a high-pressure balloon for expansion of an apparatus, the high-pressure balloon is associated with the transcatheter and is not a component of an apparatus of this invention. The high-pressure balloon is removed following delivery and expansion of the apparatus to an expanded configuration.

In one embodiment, an apparatus of this invention is for use in a patient with congestive heart failure. In one embodiment, a patient has left ventricular failure and preserved right ventricular function.

FIG. 7 illustrates one embodiment of an apparatus of this invention, comprising (a) an anchor frame for placement in the LPA; (b) a connecting section having an open weave pattern, and (c) a device frame for placement in the MPA; wherein together the anchor frame, connecting section and said device frame comprise a single entity, an apparatus frame, wherein the anchor frame comprises one section of the single entity and the device frame comprises another section of the single entity and the connecting section connects the anchor frame with the device frame section. In one embodiment, a connecting section may be flexible for example so that the apparatus may include a bend in its configuration following implantation (FIG. 4D). In another embodiment, a connecting section may be less flexible, for example so that the apparatus remains linear or somewhat linear in its configuration following implantation (FIG. 3; FIGS. 4A, 4B, 4C, 4E, 4G, and 4H; FIGS. 5A-5E; FIGS. 6A-6F; and FIG. 7)

In one embodiment, a device frame, connecting section and the anchor frame comprise Nitinol shape-memory alloy and are self-expanding, wherein the device frame comprises a flow restrictor device, comprising a toroidal balloon, preassembled onto the device frame, and wherein the anchor frame is used to position and anchor the anchor frame in the LPA, thereby positioning and anchoring the device frame within the MPA. The balloon is attached to the device frame and is further in fluid contact with a thin inflation tube, wherein the inflation tube is further attached to and in fluid contact with a subcutaneously implanted inflation port. Saline or other suitable fluid could be used to adjustably inflate the balloon.

In one embodiment, the flow restrictor comprises a toroidal shaped balloon, for example see FIG. 7, comprises a low-pressure elastomeric balloon, wherein inflation of said low-pressure elastomeric balloon is adjustable at the time of implantation and thereafter and controls the effective diameter of the main pulmonary artery (MPA) during treatment of a congestive heart failure patient with left ventricular failure and preserved right ventricular function.

Methods of Use

Figure 1B:
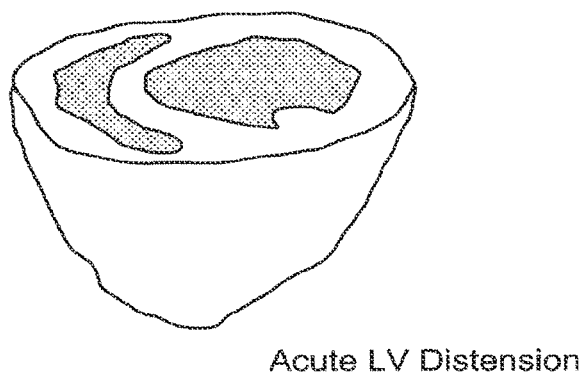

Normal cardiac contraction is a finely tuned orchestrated activity dependent of muscle function, ventricular geometry and loading conditions termed preload and afterload. When congestive heart failure (CHF) due to left ventricular systolic failure occurs it is typically associated with changes in the geometry of the ventricles. The left ventricle becomes dilated and the interventricular septum is deflected into the right ventricle (FIGS. 1A and 1B). The efficient systolic function of the left ventricle is dependent not only on the strength of the myocardium but also on the left ventricular geometry, the position and shape of the interventricular septum and the geometry and function of the right ventricle. Increasing flow resistance out of the RV has the effect of increasing pressing in the RV. This increased RV pressure may help to support and reposition the interventricular septum during systolic pumping of the LV. In one embodiment, a method of this invention affects the position and function of the interventricular septum during systole.

In one embodiment, left ventricle failure may be caused by an ischemic cardiomyopathy. In ischemic cardiomyopathy, the heart's ability to pump blood is decreased because the heart's main pumping chamber, the left ventricle, is enlarged, dilated and weak. This is caused by ischemia—a lack of blood supply to the heart muscle caused by coronary artery disease and heart attacks.

In one embodiment, a method of this invention repositions the interventricular septum to a more normal anatomical/physiological position by increasing the counter pressure of the RV on the septum wall. In one embodiment, a method of this invention for repositioning, supporting or repositioning and supporting the interventricular septum in a LV failure patient comprises implanting an apparatus of this invention, as described in detail above. In certain embodiments, the result of repositioning, supporting, or repositioning and supporting the interventricular septum results in more efficient LV pumping, thereby treating, reducing the severity of, delaying the onset of or reducing symptoms associated with congestive heart failure (CHF), or any combination thereof.

In one embodiment, a method of this invention comprises treating, reducing the severity of, delaying the onset of or reducing symptoms associated with left ventricle failure in an adult subject, said method comprising pulmonary artery banding (PAB). In another embodiment, left ventricle failure comprises ischemic left ventricular (LV) dysfunction. In another embodiment, left ventricle failure comprises chronic ischemic left ventricular (LV) dysfunction.

In one embodiment, this invention provides apparatuses, as described throughout, which may be used for treating a patient with CHF. CHF may be due to congenital heart disease, coronary artery disease, high blood pressure that is not well controlled, heart attack, heart valves that are leaky or narrowed, or infection that weakens the heart muscle, or any known cause in the art, or any combination thereof.

In one embodiment, an apparatus of this invention may be used to treat, reduce the severity of, delay the onset of, or reduce symptoms associated with any cardiac or pulmonary condition that requires blood flow reduction through a pulmonary artery. In one embodiment, a method of this invention may be used to treat, reduce the severity of, delay the onset of or reduce symptoms associated with any cardiac or pulmonary condition that requires blood flow reduction through a pulmonary artery. Pulmonary conditions that require blood flow reduction through a pulmonary artery may include conditions with excessive pulmonary blood flow in order to prevent pulmonary hypertrophy and irreversible (fixed) pulmonary hypertension. Cardiac conditions that require blood flow reduction through a pulmonary artery may include congenital heart defects such as ventricular septal defects (VSD) and atrioventricular septal defects (AVSD), wherein there may be one or multiple holes in the walls separating adjacent chambers. This causes left-to-right shunting of blood as oxygenated blood can flow back to the right side of the heart, resulting in a mixture of oxygenated and deoxygenated blood. Increased amounts of blood on the right side of the heart cause an excess of blood flow into the lungs (pulmonary circulation) and increased pulmonary resistance due to the buildup of pressure.

In one embodiment, a method of this invention is for treating, reducing the severity of, delaying the onset of or reducing symptoms associated with left ventricular failure in an adult human comprising implanting an apparatus comprising: (a) an anchor frame for placement in a branch pulmonary artery; and (b) a device frame for placement in the main pulmonary artery (MPA); and (c) a connecting section; wherein the anchor frame, and the device frame and the connecting section comprise a single entity, an apparatus frame, wherein the anchor frame comprises one section of the apparatus frame, and the device frame comprises another section of the apparatus frame, and the connecting section connects the anchor frame and the device frame of the single entity, and wherein the anchor frame is used to position the device frame within the MPA when the apparatus is in an expanded position; wherein the device frame comprises an adjustable flow restrictor; the method comprising the steps of: implanting the apparatus using transcatheter delivery such that the anchor frame resides within a branch pulmonary artery and the device frame resides within the MPA; and adjusting the flow restrictor to reduce the effective diameter of the MPA; wherein implantation of the apparatus treats, reduces the severity of, delays the onset of, or reduces symptoms associated with left ventricular failure in an adult human.

In certain embodiments, methods of this invention for treating, reducing the severity of, delaying the onset of or reducing symptoms associated with left ventricle failure in an adult subject, comprise pulmonary artery banding (PAB). In another embodiment, left ventricle failure is due to congestive heart failure. In another embodiment, left ventricle failure is due to ischemic damage. In a further embodiment, PAB comprises a reversible process.

In another embodiment, PAB comprises external PAB. In another embodiment, external PAB comprises wrapping a band around the exterior of the main pulmonary artery (MPA) and fixing the band in place. In another embodiment, an external band is fixing the band in place comprises a surgical procedure. In another embodiment, fixing the band in place comprises sutures. In another embodiment, external PAB comprises use of an inflating band ring. In another embodiment, external PAB comprises use of an adjustable band. In another embodiment, an adjustable band may be controlled remotely. In still another embodiment, external PAB comprises use of any band known in the art. In another embodiment, an external band comprises a biocompatible material.

In yet another embodiment, the PAB comprises an intravascular PAB. In another embodiment, intravascular PAB comprises use of a transcatheter delivery of a device into a pulmonary artery. In another embodiment, intravascular PAB comprises minimally invasive PAB. In another embodiment, intravascular PAB comprises use of an apparatus of this invention. In another embodiment, the PAB comprises use of an adjustable device. Examples of adjustable devices for intravascular administration are known in the art, for example see U.S. Pat. Nos. 6,120,534 and 6,638,257, which are hereby incorporated in their entirety. In another embodiment, an adjustable device comprises a balloon. In another embodiment, an adjustable band may be controlled remotely. In still another embodiment, intravascular PAB comprises use of any device known in the art. In another embodiment, an intravascular device used for PAB comprises a biocompatible material.

It will be appreciated by a skilled artisan that the term "biocompatible material" as used herein, refers to a material, synthetic or natural, and which remains in intimate contact with living tissue and which does not threaten, impede, or adversely affect living tissue.

In another embodiment, an apparatus as described herein may be used for treating, reducing the severity of, delaying the onset of or reducing symptoms associated with left ventricle failure in an adult subject.

In one embodiment, as used herein, the term "treating" refers to both therapeutic treatment and prophylactic or preventative measures, wherein the object is to prevent or lessen the targeted pathologic condition, for example CHF, as described hereinabove. Thus, in one embodiment, treating may include directly affecting or curing, suppressing, inhibiting, preventing, reducing the severity of, delaying the onset of, reducing symptoms associated with CHF, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse of CHF symptoms, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging a patient survival, or a combination thereof.

In one embodiment, a method of this invention is for treating, reducing the severity of, delaying the onset of or reducing symptoms associated with left ventricular failure in a human adult patient. In another embodiment, a method of this invention is for treating, reducing the severity of, delaying the onset of or reducing symptoms associated with congestive heart failure in a human adult patient. In another embodiment, a patient is a human child. In yet another embodiment, a patient is a human infant.

In one embodiment, an apparatus of this invention may be implanted in a patient in need. As has been described in the art, in certain embodiments, a catheter may be brought through a vein to the right atrium, through the tricuspid valve into the right ventricle, and out through the pulmonary artery to the start of the branch LPA where deployment may commence when the desired location in the LPA is identified, which ensures proper position of the device frame in the MPA.

As used herein, the term "deployment" refers in one embodiment to delivery of an apparatus of this invention to a desired location; to positioning of the apparatus within that desired position, for example the anchor frame in the LPA and the device frame in the MPA; and to expanding the apparatus at the desired position, for example using a self-expanding metallic frame or a high-pressure balloon-expanding frame; such that the device frame is anchored within the MPA. Following deployment, the catheter may be removed, including the high-pressure balloon for expansion, if used.

In one embodiment, an apparatus of this invention may be implanted using a transcatheter procedure. In one embodiment, implantation comprises implanting an apparatus frame. In another embodiment, implantation comprises implanting an apparatus frame comprising a medical device attached to the device frame as describe above. Guide wires and balloons may be included with the apparatus at the time of initial implantation or may be implanted at a later date, together or separately.

In one embodiment, an implanted apparatus may remain in place for an extended time period. In certain embodiments, the time-frame that an implanted apparatus remains in place is variable. In some embodiments, the time-frame that an implanted apparatus remains in place corresponds to the length of time, the "duration of a treatment" or the length of time treatment is needed.

As used herein, the term "duration of treatment" refers in one embodiment to a time until balloon(s) are completely deflated. Duration of treatment may be determined by a patient's state of health, LV output, position of the interventricular septum, or any combination thereof, or any other medical information determined pertinent by medical personnel.

In one embodiment, an implanted apparatus remains in place after treatment is completed. In one embodiment, an implanted apparatus remains in place indefinitely, wherein the balloon(s) comprised in a device frame are completely deflated when the duration of treatment has been completed. In one embodiment, treatment is halted, the balloon(s) deflated and the apparatus remains in place. In another embodiment, balloon(s) comprised within a device frame of implanted apparatus are removed when treatment is complete, while the apparatus frame remains in place. In another embodiment both the balloon(s) and the apparatus frame are removed when treatment is complete. In one embodiment, if a flow restrictor comprising an at least one balloon is removed, the subcutaneous port is also removed at the same time or at a later date. In another embodiment, if a flow restrictor comprising an at least one balloon remains in place in a deflated state, the subcutaneously implanted port remains in place for potential use at a later date. In yet another embodiment, if a flow restrictor comprising an at least one balloon remains in place in a deflated state, the subcutaneously implanted port is removed.

Duration of treatment may differ for each individual patient and for different therapeutic episodes for a single patient. In one embodiment, an implanted apparatus remains in place comprising balloon(s) in an inflation state, or a partially inflated state, wherein the effective change of diameter of the MPA is greater than 0% (0% being totally deflated) for a number of days, for example about 1-8 days. In another embodiment, for about a number of weeks, for example 2 weeks, 3 weeks, 4 weeks, 5 weeks, 6 weeks, 7 weeks or 8 weeks. In yet another embodiment, for a number of months, for example about 3 months, 4 months, 5 months, 6, months, 7, months, 8 months, 9 months, 10 months or 11 months. In still another embodiment, an implanted apparatus remains in place with balloon(s) in a greater than 0% inflation state for a number of years, for example about 1 year or two years or more. In another embodiment the length of treatment is indefinite, and continues for as long as there is clinical need.

In one embodiment, only a portion of the apparatus remains in place for an extended time, for example the apparatus frame. In one embodiment, balloons, guide wires, and or inflation tubes, may be implanted and/or removed over the extended implantation time of the apparatus frame.

In one embodiment, an apparatus of the invention used to treat, for example CHF, comprises a flow restrictor comprising at least one balloon, wherein the balloon comprises a low-pressure elastomeric balloon, wherein inflation of the low-pressure elastomeric balloon is adjustable and controls the effective diameter of the MPA during treatment of the CHF patient with left ventricular failure and preserved right ventricular function.

In one embodiment, an at least one inflatable balloon is inflated based on a current position of the interventricular septum of a patient. Determining the position of the interventricular septum may be through any means known in the art, for example through the use of an echocardiogram. Often, the interventricular septum of a patient suffering LV failure is distended from its more central position into the right ventricle (RV).

In one embodiment, an at least one balloon of this invention is inflated while medical personnel monitor the position of the interventricular septum. In another embodiment, an at least one balloon of this invention is inflated using step-wise adjustments, wherein medical personnel monitor the position of the interventricular septum before and/or after each step-wise adjustment. In one embodiment, an at least one inflatable balloon is inflated or deflated to a state wherein the interventricular septum is moved slightly back to midline position, closer to what is anatomically/ physiologically normal. In one embodiment, the inflation state of an at least one inflatable balloon, may result in the interventricular septum moving towards midline position, closer to what is anatomically/physiologically normal.

Typical RV pressure is about 25% of the LV pressure. Pressure may be measured by any means known in the art. For example, a small pressure sensor could be attached to the apparatus frame upstream of the medical device, which in certain embodiments may be an at least one balloon in an inflated or partially inflated state. This upstream sensor would provide the RV pressure. In another embodiment, at least two small pressure sensors could be attached to the apparatus frame, for example one upstream and one downstream of the medical device, which in certain embodiments may be an at least one balloon in an inflated or partially inflated state. The upstream sensor would provide the RV pressure, while the downstream pressure would provide the PA pressure after the flow constriction. Together, the differential pressure across the medical device restricting the flow may be determined. Alternately, pressures at different locations may be measured directly by catherization. Pressure could also be measured by echocardiogram, Doppler ultrasound, or other methods known in the art.

In some embodiments, an at least one balloon of this invention may be inflated/deflated until pressure in the RV is between 25%-99% of LV pressure. In other embodiments, an at least one balloon of this invention may be inflated/ deflated until pressure in the RV is between 50%-99% of LV pressure. In yet other embodiments, an at least one balloon of this invention may be inflated/deflated until pressure in the RV is between 50%-75% of LV pressure. In still other embodiments, an at least one balloon of this invention may be inflated/deflated until pressure in the RV is between 60%-75% of LV pressure.

Embodiments of this invention may use effective diameter of the MPA as a target for determining inflation state of a balloon.

In another embodiment, in accessing the use of an apparatus of this invention, measurements may be made based on LV cardiac output, wherein a skilled practitioner may attempt to increase LV cardiac output, potentially in a step-wise fashion, by increasing obstruction in the MPA (for example: decrease the effective diameter of the MPA by adjusting inflation of an at least one balloon).

In all scenarios, since the inflation of an at least one balloon is adjustable, skilled personnel could proceed inflating an at least one balloon in step-like fashion: for example, (1) an initial size could be set, followed by (2) a time period of observation of relevant parameters, for instance RV pressure, positioning of the interventrical septum, or other, and following observation (3) inflation state of an at least one balloon could be increased or decreased dependent on need. This process may be continued for the duration of a treatment.

In one embodiment, an apparatus of the invention used to treat CHF comprises a flow restrictor comprises more than one balloon, wherein the balloons comprise low-pressure elastomeric balloons, wherein inflation of the balloons is adjustable and controls the effective diameter of the MPA during treatment of a congestive heart failure patient with left ventricular failure and preserved right ventricular function. Methods of this invention may adjustable control the effective diameter of the MPA for a position of complete openness (0%) change in effective diameter to reduction of the effective diameter to about 40-70% or 50-70% changes, described above in detail. The skilled medical professional, in one embodiment may adjust the effective diameter of a flow restrictor, for example a toroidal balloon, in a step-wise fashion. Once implanted, the balloon could be inflated such that the effective diameter is reduced by an initial amount, for example 30%. Observation of heart function could be monitored with additional step-wise adjustments being made by the skilled medical professional.

Over time, for example with improvement observed in the patient's heart function, including a more physiological positioning of the interventricular septum, it may be determined that the flow restrictor, for example an at least one balloon, could be deflated step-wise, or completely deflated or removed in a single step.

As used herein, in one embodiment, the term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers.

As used herein, the term "comprising" is intended to mean that the apparatus includes the recited elements, but not excluding others which may be optional. By the phrase "consisting essentially of" it is meant that an apparatus that includes the recited elements but exclude other elements that may have an essential significant effect on the performance of a method of use, for example for treating CHF. "Consisting of" shall thus mean excluding more than traces of other elements from an apparatus of this invention. Embodiments defined by each of these transition terms are within the scope of this invention.

In one embodiment, the term "a" or "one" or "an" refers to at least one. In one embodiment the phrase "two or more" may be of any denomination, which will suit a particular purpose.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An in-vivo intravascular apparatus for reducing symptoms associated with left ventricle failure in a human adult comprising:
   (a) an anchor frame configured for anchoring the apparatus to a branch pulmonary artery of a human heart;
   (b) a device frame including a flow restrictor, wherein said flow restrictor is configured to increase resistance of flow flowing out from a right ventricle of the human heart; and
   (c) a connecting section connecting said device frame to said anchor frame;

(d) at least one pressure sensor attached to at least one of said anchor frame, device frame and connecting section.

2. The in-vivo intravascular apparatus of claim 1, wherein said at least one pressure sensor comprises a first pressure sensor positioned upstream from said flow restrictor.

3. The in-vivo intravascular apparatus of claim 2, wherein said first pressure sensor is configured for sensing right ventricle pressure.

4. The in-vivo intravascular apparatus of claim 1, wherein said at least one pressure sensor comprises a second pressure sensor positioned downstream from said flow restrictor, wherein said second pressure sensor senses pulmonary artery pressure.

5. The in-vivo intravascular apparatus of claim 1, wherein said at least one pressure sensor comprises:
a first pressure sensor positioned upstream from said flow restrictor; and
a second pressure sensor positioned downstream from said flow restrictor.

6. The in-vivo intravascular apparatus of claim 5, wherein said first pressure sensor is configured for sensing right ventricle pressure and said second pressure sensor is configured for sensing pulmonary artery pressure downstream from said flow restrictor.

7. The in-vivo intravascular apparatus of claim 5, wherein said first pressure sensor and said second pressure sensor are configured for sensing a differential pressure across said flow restrictor.

8. The in-vivo intravascular apparatus of claim 1, wherein the apparatus is configured to be deliverable by a transcatheter procedure.

9. The in-vivo intravascular apparatus of claim 8, wherein the apparatus is configured to be self-expandable.

10. The in-vivo intravascular apparatus of claim 8, wherein the apparatus is configured to be balloon expandable.

11. The in-vivo intravascular apparatus of claim 8, wherein said flow restrictor is configured to be manipulated in-vivo to adjust said resistance of flow post delivery.

12. The in-vivo intravascular apparatus of claim 1, wherein said flow restrictor is preassembled on said device frame.

13. A method for reducing symptoms associated with left ventricle failure in a human adult, the method comprising:
anchoring an intravascular apparatus to a branch pulmonary artery wherein said intravascular apparatus comprises a flow restrictor configured to increase resistance of flow therethrough;
increasing resistance of flow flowing out from a right ventricle of the human heart with said flow restrictor based on said anchoring, wherein said increasing resistance is configured to reduce symptoms associated with the left ventricle failure in a human adult;
sensing pressure in a vicinity of said flow restrictor after said anchoring; and
adjusting said resistance of flow affected by said flow restrictor during treatment based on said sensing.

14. The method of claim 13, wherein said sensing pressure comprises sensing pressure upstream from said flow restrictor.

15. The method of claim 13, wherein said sensing pressure comprises sensing right ventricle pressure.

16. The method of claim 13, wherein said sensing pressure comprises sensing pulmonary artery pressure downstream from said flow restrictor.

17. The method of claim 13, wherein said sensing pressure comprises sensing both right ventricle pressure upstream from said flow restrictor and sensing pulmonary artery pressure downstream from said flow restrictor.

18. The method of claim 13, wherein said sensing pressure comprises sensing a differential pressure across said flow restrictor.

19. The method of claim 13, wherein said pressure is sensed with at least one pressure sensor attached to said intravascular apparatus.

20. The method of claim 13, wherein said pressure is sensed by catherization.

21. The method of claim 13, wherein said pressure is sensed by echocardiogram or by Doppler ultrasound.

22. The method of claim 13, wherein adjusting resistance of flow is configured for repositioning an interventricular septum of said human adult.

* * * * *